US012290813B2

(12) United States Patent
Handique et al.

(10) Patent No.: US 12,290,813 B2
(45) Date of Patent: May 6, 2025

(54) APPARATUS AND METHOD FOR FAST DIGITAL DETECTION

(71) Applicant: Bio-Rad Laboratories, Inc., Hercules, CA (US)

(72) Inventors: Kalyan Handique, Ann Arbor, MI (US); Ronald Lebofsky, Kensington, CA (US); Josh Shinoff, Emeryville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 521 days.

(21) Appl. No.: 17/330,663

(22) Filed: May 26, 2021

(65) Prior Publication Data

US 2021/0370296 A1    Dec. 2, 2021

Related U.S. Application Data

(60) Provisional application No. 63/030,134, filed on May 26, 2020.

(51) Int. Cl.
| | | |
|---|---|---|
| *C12Q 1/00* | (2006.01) | |
| *B01L 3/00* | (2006.01) | |
| *B01L 7/00* | (2006.01) | |
| *C12Q 1/6806* | (2018.01) | |

(52) U.S. Cl.
CPC ......... *B01L 3/502738* (2013.01); *B01L 7/525* (2013.01); *C12Q 1/6806* (2013.01); *B01L 2200/027* (2013.01); *B01L 2200/0689* (2013.01); *B01L 2300/0816* (2013.01); *B01L 2300/0867* (2013.01); *B01L 2300/0877* (2013.01); *B01L 2400/0487* (2013.01)

(58) Field of Classification Search
CPC ........................... C12Q 1/6806; C12Q 1/6837
See application file for complete search history.

(56) References Cited

U.S. PATENT DOCUMENTS

| | | |
|---|---|---|
| 7,250,267 B2 | 7/2007 | Walt et al. |
| 7,480,433 B2 | 1/2009 | Walt et al. |
| 7,595,473 B2 | 9/2009 | Walt et al. |
| 8,460,878 B2 | 6/2013 | Walt et al. |
| 8,460,879 B2 | 6/2013 | Walt et al. |
| 9,395,359 B2 | 7/2016 | Walt et al. |
| 9,617,589 B2 | 4/2017 | Ramsey et al. |
| 10,633,693 B1 | 4/2020 | Handique et al. |
| 2004/0009583 A1 | 1/2004 | Benn et al. |
| 2012/0190590 A1 | 7/2012 | Wohlstadter et al. |

(Continued)

FOREIGN PATENT DOCUMENTS

| | | |
|---|---|---|
| WO | 2010/039179 A1 | 4/2010 |
| WO | 2010/039180 A2 | 4/2010 |

(Continued)

OTHER PUBLICATIONS

International Search Report and Written Opinion in PCT/US2021/034152 mailed Oct. 6, 2021; 18 pages.

(Continued)

*Primary Examiner* — Natalia Levkovich
(74) *Attorney, Agent, or Firm* — Kilpatrick Townsend and Stockton LLP

(57) ABSTRACT

Methods and systems for sample target molecules are provided.

20 Claims, 14 Drawing Sheets

Specification includes a Sequence Listing.

(56) References Cited

U.S. PATENT DOCUMENTS

| | | | |
|---|---|---|---|
| 2013/0115686 A1* | 5/2013 | Park | B01L 3/502 137/15.01 |
| 2016/0201054 A1 | 7/2016 | Chen et al. | |
| 2016/0288120 A1* | 10/2016 | Song | B01L 3/50853 |
| 2020/0056231 A1 | 2/2020 | Lebofsky et al. | |
| 2020/0391210 A1 | 12/2020 | Handique | |

FOREIGN PATENT DOCUMENTS

| | | |
|---|---|---|
| WO | 2011/109364 A2 | 9/2011 |
| WO | 2011/109372 A1 | 9/2011 |
| WO | 2011/109379 A1 | 9/2011 |
| WO | 2012/103447 A1 | 8/2012 |
| WO | 2012/142300 A2 | 10/2012 |
| WO | 2012/142301 A2 | 10/2012 |
| WO | 2012/170776 A2 | 12/2012 |
| WO | 2014/113502 A1 | 7/2014 |
| WO | 2014/183096 A1 | 11/2014 |
| WO | 2016/115256 A1 | 7/2016 |
| WO | 2016/130923 A1 | 8/2016 |
| WO | 2018/222585 A2 | 12/2018 |
| WO | 2019/060607 A1 | 3/2019 |
| WO | 2019/199865 A1 | 10/2019 |
| WO | 2019/199869 A1 | 10/2019 |
| WO | 2019/199871 A1 | 10/2019 |

OTHER PUBLICATIONS

Robledo, R. et al.; "TaqMan genotyping of insertion/deletion polymorphisms"; *Methods in Molecular Biology*; vol. 311; 2005; pp. 165-176.

\* cited by examiner

APPARATUS AND METHOD FOR FAST DIGITAL DETECTION

CROSS-REFERENCE TO RELATED PATENT APPLICATIONS

The present patent application claims benefit of priority to U.S. Provisional Patent Application No. 63/030,134, filed May 26, 2020, which is incorporated by reference for all purposes.

REFERENCE TO A SEQUENCE LISTING

The instant application contains a Sequence Listing which has been submitted electronically in ASCII format and is hereby incorporated by reference in its entirety. Said ASCII copy, created on Feb. 26, 2025, is named 094868-1250573_117710US_SL.txt and is 1,247 bytes in size.

BACKGROUND OF THE INVENTION

US published patent application 2007/0281311, to Roth et al, describes a system for measuring emission from microspheres or beads coupled to fluorescent dyes or tags, where the fluorescent dyes or tags indicate or are approximately proportional to a biological reaction. The beads are magnetic, and are immobilized by a magnet in an imaging volume, while they are being imaged by a CCD, many beads at a time. The system is compared to a prior art system using a flow cytometer, in which fluorescent particles are detected serially, one at a time, which is said to be described in U.S. Pat. No. 5,981,180 to Chandler et al.

US published patent application 2007/0064990 to Roth, describes methods of image processing for analyzing images of fluorescent particles, including methods of analyzing a first image of particles having a uniform concentration of fluorescence material, and a second image of particles having an unknown concentration of a fluorescence material.

BRIEF SUMMARY OF THE INVENTION

In some embodiments, a method of detecting a target nucleic acid in multiple samples is provided. In some embodiments, the method comprises:
contacting different samples comprising sample nucleic acids with different pluralities of solid supports to form different mixtures,
  wherein the solid supports comprise a plurality of capture molecules that bind to the sample target nucleic acid or a vehicle comprising the sample target nucleic acid, and
wherein the solid supports contacted to different samples have a characteristic distinguishable from other solid supports contacted to different samples;
binding the capture molecules to the target nucleic acids or vehicles comprising the target nucleic acids, wherein the number of solid supports in the mixture is sufficiently high that at least some solid supports are not bound to target nucleic acids or vehicles comprising target nucleic acids;
combining the different mixtures to form a bulk mixture;
introducing the solid supports comprising bound target nucleic acids or vehicles into an array of wells, wherein the wells each can contain one but no more than one solid support or wherein the wells can contain more than one (e.g., no more than 2, 3, 4, 5 or more) solid support;
detecting in each well (i) the presence or absence of the sample nucleic acids and (ii) the characteristic of the solid support; and
determining the number of target nucleic acids per sample wherein the determining comprises determining the number of wells having detected sample nucleic acids, wherein the sample identity is determined by the detected characteristic of the solid support. In some embodiments, the determining also comprises determining the number of wells lacking detected sample nucleic acids. In some embodiments, the determining also comprises determining the number of beads in a well.

In some embodiments, the plurality of capture molecules on a solid support are identical.

In some embodiments, after the binding and before or after the combining, washing unbound sample components from the solid supports.

In some embodiments, the wells comprise affinity agents that bind the target nucleic acids or vehicles comprising target nucleic acids to the well.

In some embodiments, after the introducing, the wells are covered. In some embodiments, the wells are covered by oil, a gel, or a solid clear lid, or an elastomeric lid or an adhesive coated flexible film. In some embodiments, the sample target nucleic acids are amplified. In some embodiments, after the sample target nucleic acids are amplified, the sample target nucleic acids are attached to the wells via an affinity agent linked to the wells.

In some embodiments, the solid supports are beads. In some embodiments, the beads are between 0.1-100 µm (e.g., 1-50 µm) in diameter.

In some embodiments, the characteristic is the color of the solid support.

In some embodiments, following the introducing and before the detecting, amplifying the sample nucleic acids hybridized to the capture oligonucleotides, and wherein the detecting comprises detecting signal from a reagent in the wells that changes based on the presence or absence of amplified nucleic acids. In some embodiments, the amplifying is loop-mediated isothermal amplification (LAMP). In some embodiments, the signal is fluorescence. In some embodiments, the reagent is a double-stranded binding dye, a hydrolysis probe, a hybridization probe, or a CRISPR/CAS protein and a labeled probe that is cleaved upon collateral cleavage by the CRISPR/CAS protein.

In some embodiments, the detecting comprises introducing a probe that specifically binds to a first target nucleic acid and detecting specific binding of the probe to the first target nucleic acid. In some embodiments, the method further comprises washing away the probe from the well and then introducing a second probe that specifically binds to a second target nucleic acid and detecting specific binding of the second probe to the second target nucleic acid.

In some embodiments, the sample contains cells or viruses.

In some embodiments, the target nucleic acids are RNA. In some embodiments, the RNA is reverse transcribed into cDNA. In some embodiments, the RNA is reverse transcribed before the introducing. In some embodiments, the RNA is reverse transcribed after the introducing.

In some embodiments, the array of wells is a slide comprising 10,000-10,000,000 wells.

In some embodiments, the array of wells are of multiple different sizes or volumes. In some embodiments, the solid supports are beads having diameters no less than 10% smaller than the diameter of well openings.

In some embodiments, the ratio of the diameter of the solid support to the diameter of the well is 1:1, or 1:2, or 1:3, or 1:4.

In some embodiments, sets of wells are separated from each other such that individual samples can be deposited in each. In some embodiments, the sets of wells are separated by a vertical splash shield.

In some embodiments, the wells have an opening that is hexagonal.

In some embodiments, all of the solid supports contacted to a sample have identical capture molecules.

In some embodiments, the solid supports contacted to the sample are of at least two types, wherein a first type comprises capture molecules that bind to a first sample target nucleic acid or a vehicle comprising the first sample target nucleic acid and a second type comprises capture molecules that bind to a second sample target nucleic acid or a vehicle comprising the second sample target nucleic acid.

In some embodiments, the number of solid supports in the mixture is more than the number of target nucleic acids in the sample.

In some embodiments, the capture molecules are oligonucleotides complementary to the sample target nucleic acid and the binding comprises hybridization.

In some embodiments, the vehicle comprising the sample target nucleic acid is a cell, a virus, or a particle.

Also provided is a method of detecting a target nucleic acid in multiple samples, the method comprising contacting different samples comprising sample nucleic acids with different pluralities of solid supports to form different mixtures, wherein the solid supports comprise a plurality of capture molecules that bind to the sample target nucleic acid or a vehicle comprising the sample target nucleic acid, optionally wherein the plurality of capture molecules on a solid support are identical;

binding the capture molecules to the sample target nucleic acids, wherein the number of solid supports in the mixture is sufficiently high that at least some solid supports are not bound to target nucleic acids or vehicles comprising target nucleic acids;

optionally washing unbound sample components from the solid supports;

introducing the solid supports comprising bound sample target nucleic acids or vehicles comprising sample target nucleic acids into an array of wells, wherein the wells each can contain no more than one solid support or wherein the wells can contain more than one (e.g., no more than 2, 3, 4, 5 or more) solid support, wherein the position of wells receiving the sample beads is recorded such that wells corresponding to different samples is recorded;

detecting in each well (i) the presence or absence of the sample target nucleic acids and (ii) the position of the wells; and determining the number of target nucleic acids per sample wherein the determining comprises determining the number of wells having detected sample nucleic acids, wherein the sample identity is determined by the position of the wells. In some embodiments, the determining also comprises determining the number of wells lacking detected sample nucleic acids. In some embodiments, the determining also comprises determining the number of beads in a well.

In some embodiments, the method comprises washing unbound sample components from the solid supports, e.g., between the binding and the introducing.

In some embodiments, sets of wells are separated from each other such that individual samples can be deposited in each. In some embodiments, the sets of wells are separated by a vertical splash shield.

In some embodiments, the wells comprise affinity agents that bind the target nucleic acids or vehicles comprising target nucleic acids to the well.

In some embodiments, after the introducing, the wells are covered. In some embodiments, the wells are covered by oil. In some embodiments, the sample target nucleic acids are amplified. In some embodiments, after the sample target nucleic acids are amplified, the sample target nucleic acids are attached to the wells via an affinity agent linked to the wells.

In some embodiments, the solid supports are beads.

In some embodiments, the beads are between 0.1-100 μm (e.g., 1-50 μm) in diameter.

In some embodiments, following the introducing and before the detecting, amplifying the sample nucleic acids hybridized to the capture oligonucleotides, and wherein the detecting comprises detecting signal from a reagent in the wells that changes based on the presence or absence of amplified nucleic acids. In some embodiments, the amplifying is loop-mediated isothermal amplification (LAMP). In some embodiments, the signal is fluorescence. In some embodiments, the reagent is a double-stranded binding dye, a hydrolysis probe, a hybridization probe, or a CRISPR/CAS protein and a labeled probe that is cleaved upon collateral cleavage by the CRISPR/CAS protein.

In some embodiments, the detecting comprises introducing a probe that specifically binds to a first target nucleic acid and detecting specific binding of the probe to the first target nucleic acid In some embodiments, the method further comprises washing away the probe from the well and then introducing a second probe that specifically binds to a second target nucleic acid and detecting specific binding of the second probe to the second target nucleic acid.

In some embodiments, the sample contains cells or viruses.

In some embodiments, the target nucleic acids are RNA. In some embodiments, the RNA is reverse transcribed into cDNA. In some embodiments, the RNA is reverse transcribed before the introducing. In some embodiments, the RNA is reverse transcribed after the introducing.

In some embodiments, the array of wells is a slide comprising 10,000-10,000,000 wells In some embodiments, the wells have an opening that is hexagonal.

In some embodiments, all of the solid supports contacted to a sample have identical capture molecules.

In some embodiments, the solid supports contacted to the sample are of at least two types, wherein a first type comprises capture molecules that bind to a first sample target nucleic acid or a vehicle comprising the first sample target nucleic acid and a second type comprises capture molecules that bind to a second sample target nucleic acid or a vehicle comprising the second sample target nucleic acid.

In some embodiments, the number of solid supports in the mixture is more than the number of target nucleic acids in the sample.

In some embodiments, the capture molecules are oligonucleotides complementary to the sample target nucleic acid and the binding comprises hybridization.

In some embodiments, the vehicle comprising the sample target nucleic acid is a cell, a virus, or a particle.

Also provided is an automated system for detecting target nucleic acids from samples. In some embodiments, the system comprises one or more of:
a first station configured to contain an array of sample processing receptacles,
a second station configured to contain an array of wells, the second station coupled to a fluid delivery system, a thermal system and a detection system, wherein the wells are configured to capture only one bead in each well,
a transfer system configured to transfer beads from the first station to the second station, and a computer processor,
wherein the second station is configured to capture the plurality of the beads into the array of wells wherein only one bead is captured in each well,
wherein the fluid delivery system is configured to deliver target nucleic acid amplification and detection reagents from reagent reservoirs into the wells,
wherein the thermal system is configured to perform an isothermal or thermocyclic amplification reaction in the wells,
wherein the detection system is configured to image the array of wells and count the wells with a detectable target nucleic acid product, and
and the computer processer is configured to receive signal from the detection system and associates the count with the sample from which the bead was associated in the first station.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to two-primer methods such as polymerase chain reaction (PCR); ligase methods such as DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are 0, or fewer than 2 or 3 complementarity mismatches over at least about 12, 14, 16, 18, or 20 contiguous nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

BRIEF DESCRIPTION OF THE DRAWINGS

FIG. 5 shows the deck of a system showing various consumables used to process 96 clinical samples at the same time.

FIG. 9 shows a microwell array slide.

DETAILED DESCRIPTION OF THE INVENTION

Introduction

Figure 1:
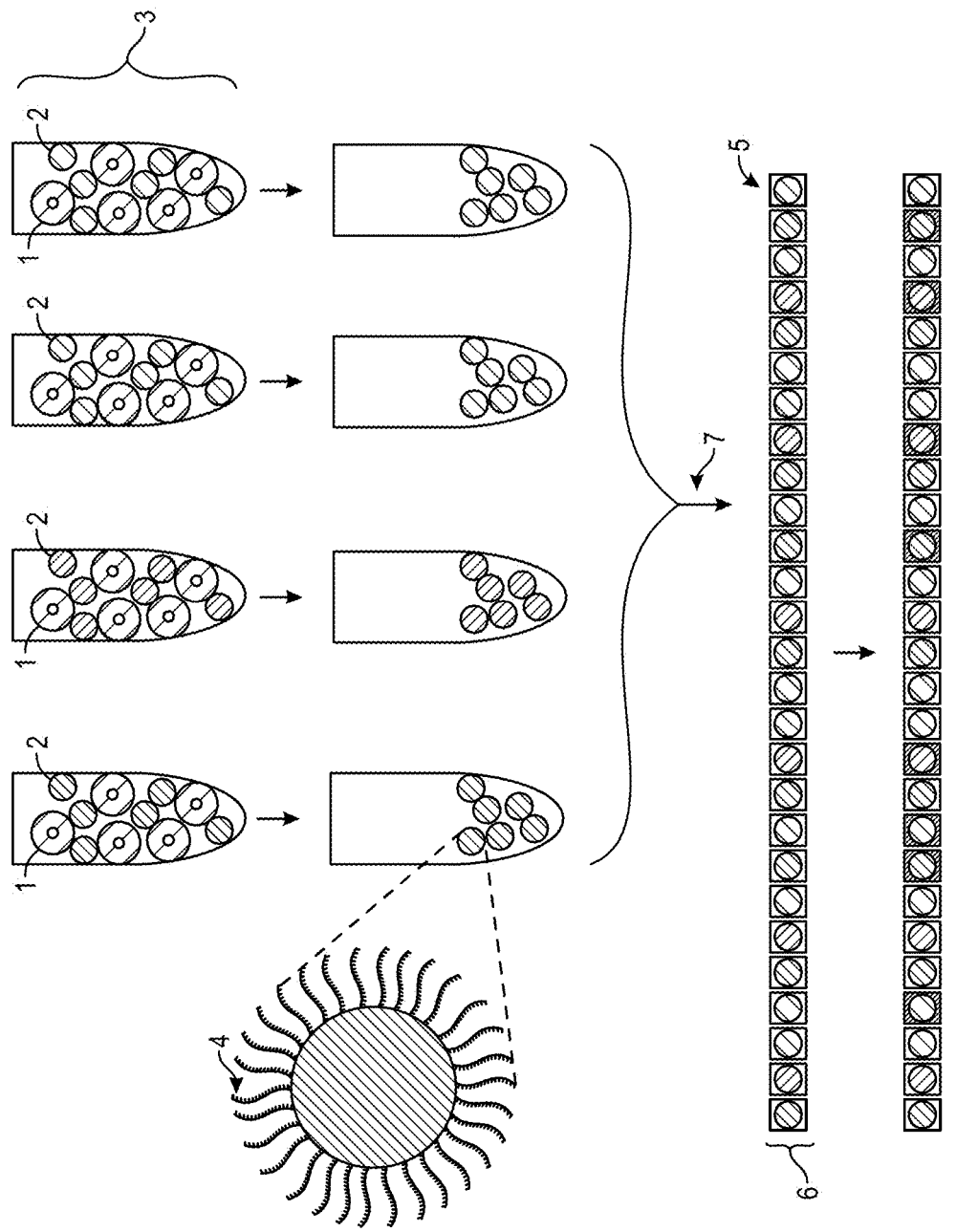
FIG. 1 depicts a work flow in which different samples (1) are mixed with different beads (2) having different color in separate receptacles (3). Oligonucleotides (4) on the beads are hybridized to nucleic acids in the sample and then the mixtures are combined into one bulk mixture. Beads (2) from the bulk mixture are subsequently introduced into separate wells (5) in an array (6) where the target nucleic acids are amplified and detected along with the color of the beads within the wells.
Figure 2:
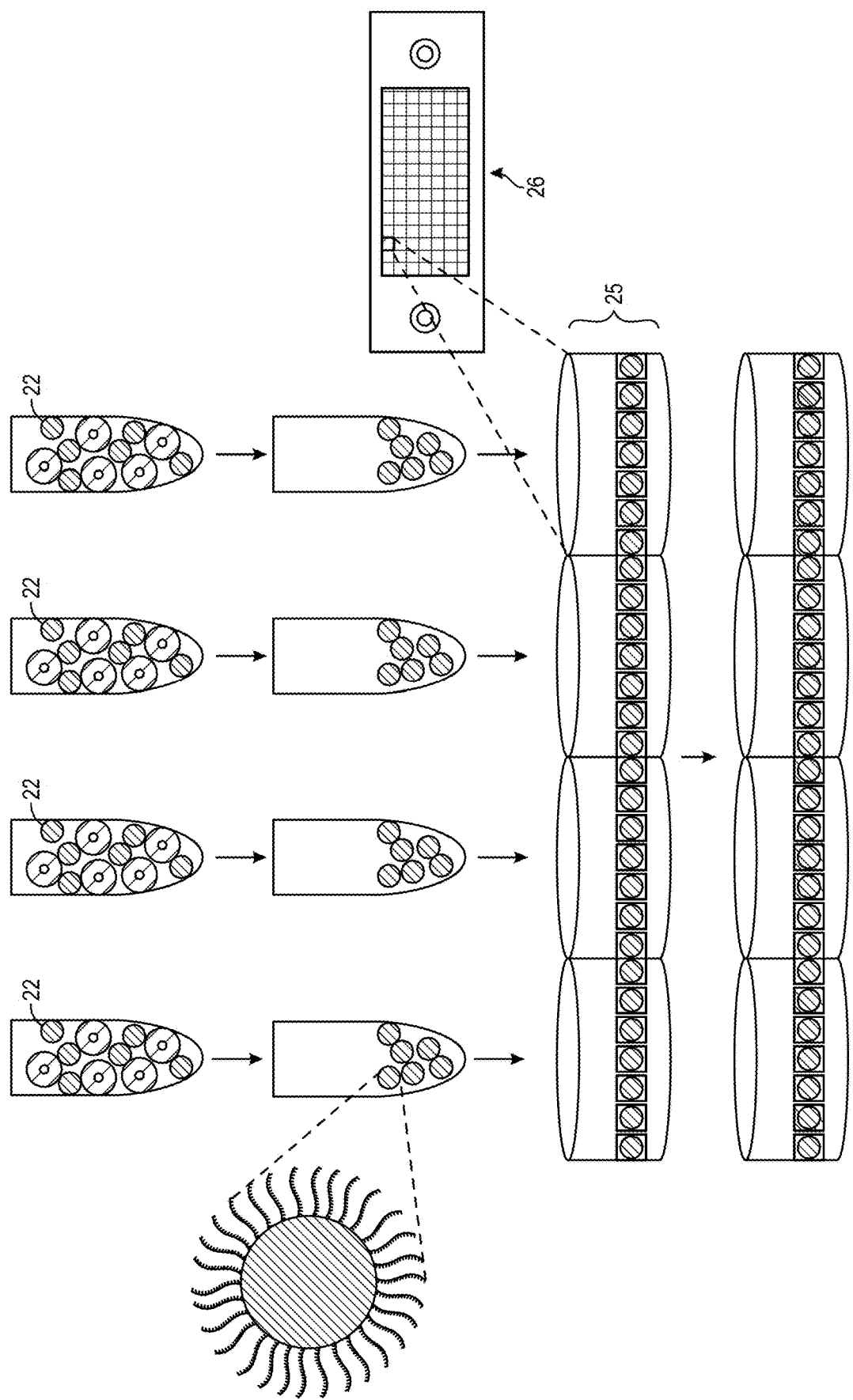
FIG. 2 depicts a workflow similar to FIG. 1 except instead of different color beads, the beads (22) are the same and a bulk mixture is not formed. Instead the address of beads from each sample is recorded in the wells (25) of the array (26) such that signal from a particular well can be matched to an origin sample.
Figure 3:
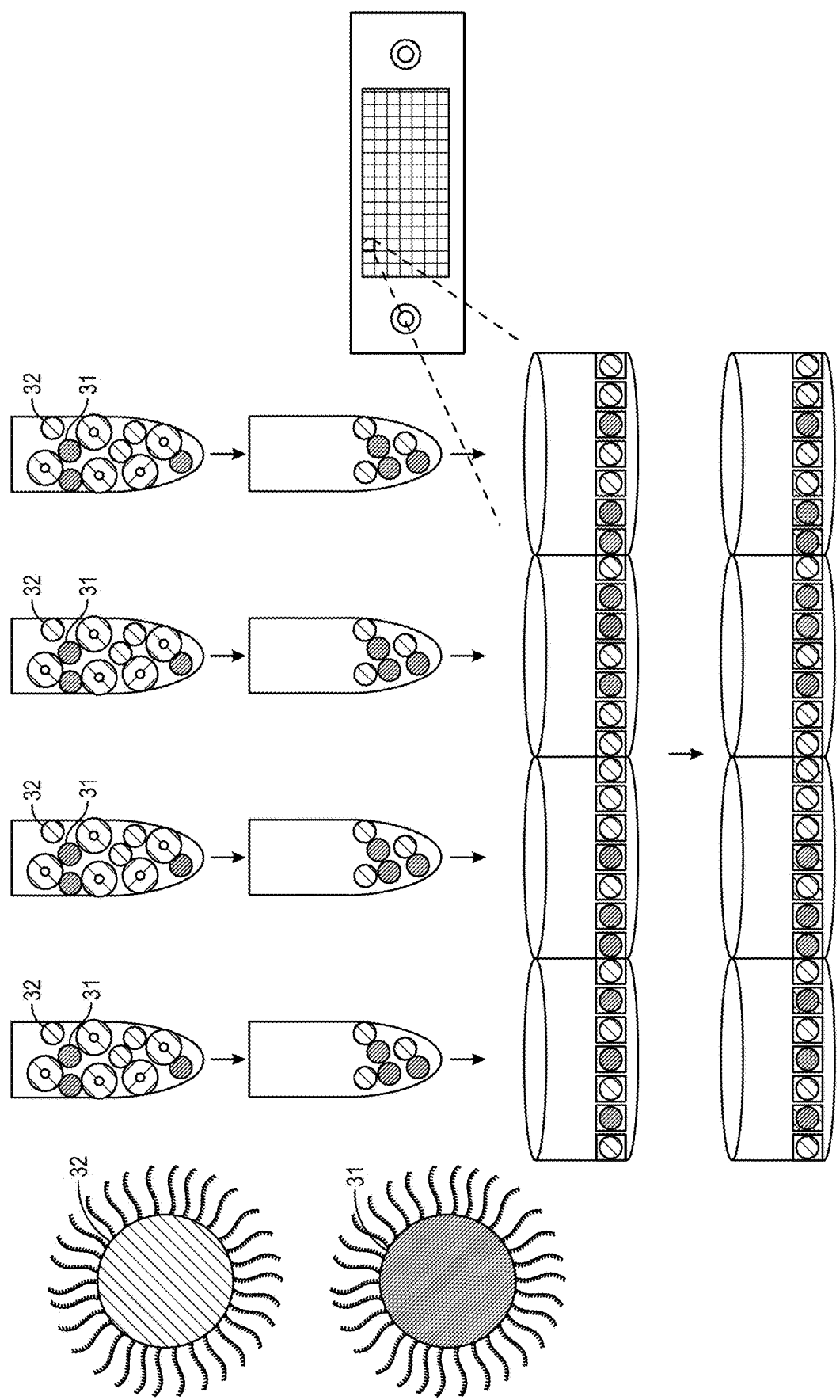
FIG. 3 depicts an embodiment similar to FIG. 2 but two different beads (31 and 32) are introduced into each sample, where the two beads have different capture molecules to capture different target molecules. The different beads can be distinguished by a characteristic, e.g., bead color.

The inventors have discovered a rapid method for detection of target molecules which can include simultaneous detection from multiple samples. Solid supports linked to capture molecules can be contacted with individual samples to bind sample target molecules. The number of solid supports can be selected such that some solid supports remain empty (not bound), for example but not limited to because there are more solid supports than target molecules. This allows for digital (i.e., present or absent) binding of target molecules to the solid supports. The solid supports binding the target molecules can then be introduced into an array of wells such that each well contains no more than one solid support. In another embodiment where samples are directed to physical locations on the array, solid supports binding the target molecules can be introduced into an array of wells such that each well contains one or more solid support. The array of wells can be assayed for the presence or absence of the target nucleic acid using any number of detection assays. The number of positive wells per sample indicate the number of targets in the original sample using Poisson distribution statistics.

A number of samples can be assayed simultaneously. In one aspect, different samples are contacted with different solid supports having characteristics that can be distinguished from each other in a later stage. This aspect allows one to combine the solid supports having bound target molecules in bulk and optionally manipulated together, and then added to the wells in the array of wells. The differing characteristics of each sample solid support can be used to determine the sample origin of the molecules in a well. Alternatively, differing characteristics of the solid supports is not required, in which the case the different sample solid supports having bound target molecules are not mixed together but are applied to the array in such a way that the location in the array for each sample is known, allowing for determination of sample origin in the array based on address (location) in the array. Where the location in the array for each sample is known, allowing for determination of sample origin in the array based on address (location) in the array, more than one solid support can be loaded into each well.

Any sample having or suspected of having a target molecule to be assayed can be used in the methods described herein. In some embodiments, the sample comprising target nucleic acids is a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc. In some embodiments, the sample is a sample comprising cells. In some embodiments, the sample is a sample containing cell-free nucleic acids (DNA, RNA) or cell-free exosomes (including but not limited to exosomes that can be derived from plasma, serum or urine. In some embodiments, the sample can be environmental samples such as waste water, treatment plant water, well water. In some embodiments, the sample can be a processed food sample such as meat products, vegetables, cheese or ground seeds.

The methods and systems described herein allow for simultaneous manipulation and assay of multiple samples. This can be achieved for example by linking target molecules from samples with the solid supports as described herein and then tracking the target molecules from different samples based on the identity of the different solid supports. Alternatively, this can be achieved by locating solid supports binding sample target molecules in specific known locations (e.g., an "address") in the array of wells such that signal from specific locations can be tracked to a sample.

Each sample can be separately mixed with solid supports in a separate receptacle. The solid supports are linked to capture molecules that bind to sample target molecules. In some embodiments, receptacles can be provided that are preloaded with the solid supports linked to the capture molecules. Alternatively, one can add the solid supports linked to the capture molecules to a sample in a receptacle. Optionally, additional components can be added to the mixture to improve binding of the capture molecules to the sample target molecules or vehicles containing the sample target molecules. For instance, in one example, one or more cell or virus lysis reagent can be added to the mixture to release cell or virus content. A buffer, salt or other excipients can also be included in the mixture. Crowding agents such as PEG may be used. Denaturants such as guanidine thiocyanate can be added to solubilize the mixtures. Proteinase K, ionic detergents and non-ionic detergents can be added to cleave the amino acids in the mixture. Non-specific absorption to surfaces can also be prevented by using the following additives: BSA, non-polyadenylated transfer RNA, random sequence oligonucleotides, and homopolymers of polynucleotides, for example. Molecular biology reactions may occur to improve the stability of the captured substrates to the solid support such as, reverse transcription, DNA extension, ligation, and tagmentation.

Any sort of solid support can be used that can be later delivered into wells in an array as discussed below. Exemplary solid supports are beads, e.g. microspheres or other particles. Solid supports suitable for attaching oligonucleotides or other capture molecules thereto include controlled pore glass (CPG) (available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, silica, glass, agarose, alginate, Poros—a copolymer of polystyrene/divinylbenzene, or reversibly cross-linked acrylamide, or polymer blends thereof. Solid supports may be combination of different materials such as gel beads containing smaller microparticles of different materials. In some embodiments, the composite support material can be gel bead of certain diameter (e.g., 20-50 micron) but containing a plurality of micro-sized magnetic particles. In some embodiments, the composite support material can b a gel bead (e.g., 20-50 micron) containing a plurality of sub-micron-sized nanoparticle-containing affinity molecules. Solid supports may be gel bead coated with an affinity layer on the surface. In some embodiments, the solid support are polyacrylamide beads with reversible crosslinks for example such as those based on Bac (N,N'-Bis(acryloyl) cystamine). Many other solid supports are commercially available and amenable to use in attaching oligonucleotides thereto. Solid supports may also have molecules bound onto the surface that have affinity for nucleic acids such a poly-lysine, polyethylenimine, polyamidoamine, histidine, N-2-acetamido-2-aminoethanesulfonic acid (ACES), N-2-acetamido-2-iminodiacetic acid (ADA); N,N-bis2-hydroxyethyl-2-aminoethanesulfonic acid (BES); N,N-bis-2-hydroxyethylglycine (BICINE); bis-2-hydroxyethyliminotrishydroxymethylmethane (Bis-Tris); 1,3-bistrishydroxymethylmethylaminopropane (Bis-Tris Propane); 3-N,N-bis-2-hydroxyethylamino-2-hydroxypropanesulfonic acid (DIPSO); 2-hydroxyethylpiperazine-N-3-propanesulfonic acid (EPPS);2-hydroxyethylpiperazine-N-4-butanesulfonic acid (HEPBS);2-hydroxyethylpiperazine-N-2-ethanesulfonic acid (HEPES); 2-hydroxyethylpiperazine-N-2-propanesulfonic acid (HEPSO); 2-N morpholinoethanesulfonic acid (MES); 4-N-morpholinobutanesulfonic acid (MOBS); 3-N-morpholinopropanesulfonic acid (MOPS); 3-N-morpholino-2-hydroxypropanesulfonic acid (MOPSO);piperazine-N—N-bis-2-ethanesulfonic acid (PIPES); piperazine-N—N-bis-2-hydroxypropanesulfonic acid (POPSO); N-trishydroxymethyl-methyl-3-aminopropanesulfonic acid (TAPS); 3-N-trishydroxymethyl-methylamino-2-hydroxypropanesulfonic acid (TAPSO);N-trishydroxymethyl-methyl-2-aminoethanesulfonic acid (TES); N-trishydroxymethylmethylglycine (TRICINE); trishydroxymethylaminomethane (Tris); polyhydroxylated imidazoles; and triethanolamine dimers. Surface coatings can also include, but are not limited to, metals such as gold, silver, steel, aluminum, silicon, and copper or non-metals such as graphite, carbon nanotube, graphene, etc.

In some embodiments, the solid support is a bead (e.g., silica gel, glass (e.g., controlled pore glass), magnetic bead, plastic, metal, polystyrene, or polymer bead). In some embodiments, the bead has a size of about 1 µm to about 100 µm in diameter. Bead diameters may be selected based on the sizes of the partitions (e.g., the sizes of microfluidic channels or droplets as discussed herein).

Beads comprising oligonucleotides conjugated to a solid support surface, including barcode-labeled oligonucleotides, and methods of making such particles, are known in the art. See, e.g., U.S. Pat. No. 6,133,436; US 2011/0028334; and International Application No. PCT/US2015/037525, incorporated by reference herein.

In some embodiments, the beads have a diameter of between 0.1-100 microns, e.g., 1-50 microns. As noted herein, the side of the solid support and the well opening are selected such that only one solid support fits within a well of the array. In some embodiments, the bead is of sufficient density to settle at the bottom of a well in aqueous solution and remain while liquid (e.g., oil) is flowed over the opening of the wells. In some embodiments, the bead is buoyant and magnetic allowing it to be pulled down using a magnet but released and allowed to float up against gravity upon release of the magnetic force.

Capture molecules can be attached to the solid support in any way convenient. In some embodiments, an intervening linker moiety can be used to link the capture molecule to the solid support. In some embodiments, linker molecules can be PEG molecules or dendrimers. Linker molecules may also have a cleavable moieties attached to it between the linker and the nucleic acid binding moieties. Oligonucleotides, for example, can be conjugated to polymer moieties that are substrates for gel-polymerization, such as acrydite. Biotinylated oligonucleotides can bind directly to streptavidin conjugated beads. In some embodiments, the capture molecule is attached to the solid support via "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001).

Any molecule that can bind a target molecule can be used. In embodiments in which the target molecule is a nucleic acid, the capture molecule can be a polynucleotide, e.g., an oligonucleotide. The oligonucleotide can be of any length. In some embodiments, the oligonucleotide is 5-500 or 5-100 nucleotides long. An oligonucleotide can include a capture sequence that is partially or fully complementary to the target nucleic acid. The capture sequence can be of appropriate length and complementarity to hybridize to the target nucleic acid under the conditions of the method. In some embodiments, the capture sequence has at least 5, 7, 9, 10, 12, 15, 20 or more contiguous or noncontiguous nucleotides complementary to the target nucleic acid. In some embodiments, where mRNA are the target nucleic acid, the capture sequence can be a polyT sequence. In some embodiments, the capture sequence is a random sequence or a gene-specific sequence. In some embodiment, nucleic acids are captured by molecules that present a positive charge at a certain acidic pH and nucleic acids released at a neutral or alkaline pH. In some embodiments, nucleic acids are RNA only. In some embodiments, nucleic acids comprise interspersed DNA and RNA nucleotides. In some embodiments, the capture oligonucleotides are blocked on the 3' end, for example, by an inverted T. In some embodiments, capture oligonucleotides may contain LNA, PNA and/or MGB motif.

In other embodiments, the capture molecule can be a protein, polysaccharide, an aptamer, or other chemical moiety that binds the target. For example, the protein can be an antibody that specifically binds to the target molecule. In some embodiments, the capture molecule can comprise streptavidin that binds to a biotinylated target molecule. In some embodiments, the capture molecule can comprise biotin that binds to a streptavidin conjugated target molecule. In some embodiments the capture molecule can be an antigen that binds to an antibody presented on the cell surface.

In some embodiments, the capture molecule is selected to specifically capture a target molecule. For example, a specific nucleotide sequence or protein. In other embodiments, the capture molecule is selected to capture a class of molecules (having a common structural feature), e.g., all nucleic acids, mRNAs having polyA sequences, all proteins of a certain class, etc.

In many embodiments, capture molecules attached to a solid support will occur in multiple copies. In some embodiments, all of the capture molecules on a particular solid support will be identical. Different solid supports can in some embodiments be attached to identical copies of the same capture molecule, i.e., such that all solid supports contacted to a sample have multiple copies of only one capture molecule. In other embodiments, different solid supports contacted to the same sample will have different capture molecules. For example, a sample could be contacted with a first solid support (or multiple first solid supports) with identical capture molecules for target A and a second solid support (or multiple second solid supports) with identical capture molecules for target B, such that targets A and B will be captured by the solid supports. Alternatively, solid supports can each include two or more different (binding different targets binding molecules. In this aspect, a solid support would have for example a binding molecule (or a plurality thereof) that binds to target A and a separate binding molecule (or a plurality thereof) that binds to target B. In another embodiment, the solid support not only has molecules used to capture nucleic acids from lysate either using specific or non-specific binding, but the solid support also has target specific forward and reverse primers that would allow performing bridge amplification on the surface of microsphere.

As noted herein, in some embodiments, the solid supports contacted to different samples have different detectable characteristics such that the characteristic can be used to track to which sample the solid support was contacted. In some embodiments, the characteristic can be assessed by visual inspection, optionally with a camera and/or scanner. For example, in some embodiments, the solid supports are of different color or reflect light at different wavelengths such that solid supports contacted to different samples can be visually detected and differentiated. The differentiation parameters may arise from size, composition, physical characteristics that affect light scattering, excitable fluorescent or colored dyes that impart different emission spectra and/or scattering characteristics to the beads, or different concentrations of one or more fluorescent dyes. When the differentiation parameter is a fluorescent dye or color, it can be coated on the surface of the beads, embedded in the beads, directly bound to molecules (e.g., capture molecules) of the solid support material, or indirectly bound to molecules (e.g. capture molecules) of the solid support material. For example, fluorescent oligonucleotides that are complementary to the capture molecules, may bind to the capture molecules in a covalent or reversible fashion. In another embodiment, a single color is used but with different step-like fluorescent intensities for each sample batch. In some embodiments, a combination of colors per single solid supports including different step intensities are used to create a bead color signature. In some embodiments, the fluorescence has a different quenching rate during illumination to distinguish different sample batch bead types In some embodiments, the solid supports are conjugated to or comprise a fluorescent semiconducting polymer dot (pdot), allowing for one to distinguish different solid supports. Examples of such pdots are described in, e.g., Wu, C., et al., *Chem. Mater.* 21:3816-3822 (2009); Rahim, N. A. A., et al., *Adv. Mater.* 21:3492-3496 (2009), Rong et al., *ACS Nano* 7(1):376-84 (2013); patent publications US 2013/0266957; WO 2012/054525; and US 2012/0282632. Chromophoric pdots can be generated by collapsing polymers into a stable sub-micron sized particle. The pdot nanoparticles provided herein may be formed by any method known in the art for collapsing polymers, including without limitation, methods relying on precipitation, methods relying on the formation of emulsions (e.g. mini or micro emulsion), and methods relying on condensation. The pdot nanoparticle size is dependent on the molecular weight of the polymer used to generate the pdots (see, for example, Zhang, Y., et al., *Chem Sci.* 6(3):2102-2109 (2015) and U.S. Pat. No. 9,382,473).

In embodiments in which the solid supports for different samples have different characteristics, following contacting of the different solid supports to different samples and binding target molecules in the sample to the capture molecules on the solid supports, the solid supports bound to the target molecules via the capture molecules can be combined into a bulk mixture. Because the different solid supports can be linked back to the samples to which they were contacted in view of the different characteristic, one can track from which sample each bead came. As the solid supports are later placed in separate wells, each bead can be assayed separately.

As an alternative to using solid supports that have distinguishing characteristics, in some embodiments the solid supports are identical or at least substantially the same. In these aspects, following capture of target molecules for each sample, the solid supports from different samples remain separate from each other (they are not mixed) and any reaction or manipulations of the captured target molecules can be done in parallel. Beads from each sample, following any processing, are placed in known locations in the wells of the array (discussed in more detail below), such that the address of these locations indicate the sample from which the target molecules were obtained.

As noted herein, a plurality of solid supports having capture molecules is contacted to each sample. The number of solid supports used will be selected such that following contact with the sample, some solid supports will remain without a bound target molecule. This can be achieved for example by using more beads than target molecules. Alternatively, due to Poisson distribution of binding agents to each other, in some embodiments, fewer beads are used than target molecules but some solid supports in practice will be bound to multiple target molecules in a Poisson distribution.

Upon mixing of the sample with the solid supports attached to capture molecules, the mixture can be incubated under conditions to allow for binding of the capture molecules to the target molecules in the sample. For example, in some embodiments, the conditions allow for hybridization of a capture oligonucleotide to a target nucleic acid. The sample can be introduced to a receptacle, which can be pre-packaged, that contains the solid supports attached to the capture molecules, and optionally a solution containing buffers, salts or other components that promote binding. In some embodiments, the receptacles can include additional ingredients such as reagents such as detergents (NP-60, SDS, Tween, Triton X-100, etc), denaturants (UREA, guanidine thiocyanate, formamide), reducing agents (DTT, TCEP), enzymes (Labiasem lysostaphin, lysozyme, Achromopeptidases, Lyticase, proteinase-K, DNases) and sample conditioning molecules (EDTA, ions, BSA, carrier nucleic acids, PEGs) that lyse cells or assist in target molecule binding to solid supports in the sample.

In some embodiments, the capture molecules bind to a vehicle that comprises or contains the target molecules. For example, a vehicle can be a synthetic construct such as beads, e.g., a hydrogel, droplets, branched polymers, or cross-linked DNA/protein structures, or a natural vehicle, which can include but are not limited to a cell, virus, or exosome.

Once the capture molecules on the solid supports have captured the target molecules (or vehicles comprising the target molecules), and optionally the solid supports from different samples (e.g., 2, 5, 3, 5, 10, 20, 50, 96, 384, 1536 or more) have been combined, the solid supports are delivered to one or more array of wells such that the solid supports are placed in the wells of the array. The solid supports can be delivered to the wells substantially as cells are delivered to wells as described in, e.g., U.S. Pat. Nos. 9,103,754 and 10,391,493. Individual solid support capture is preferably achieved by flowing or dispensing an aliquot containing a group of solid supports (with the captures target molecules) within a fluid layer over the array of wells in a direction parallel (e.g., substantially parallel, within 0.1 degrees of parallel, within 1 degree of parallel, within 45 degrees of parallel, completely parallel, etc.) to the broad surface of the substrate, and capturing the solid supports once they have descended through the fluid layer towards the array of wells under the influence of gravity. Alternatively, individual solid supports capture can be achieved by delivering an aliquot containing a group of single solid supports into a fluid layer provided by a fluid reservoir, over the array of wells in a direction perpendicular to the broad surface of the substrate, and capturing the solid supports once they have descended through the fluid layer towards the array of wells under the influence of gravity or magnetic force. However, in some variations, individual solid supports capture can additionally or alternatively be achieved by any suitable mechanism for promoting single solid supports transfer into a well of the set of wells. Furthermore, the system is optionally configured to prevent undesired fluid currents that can lift solid supports from the substrate or move solid supports from well cavities at which the solid supports are captured and fully retained within. However, in some variations, the system can be configured to facilitate moving of solid supports in any suitable manner. The flow path of a fluid through the system is preferably multidirectional and uniform, such that each solid support in the system experiences consistent conditions (e.g., gradient length scales along the flow path of flow properties such as pressure, density, temperature, solution composition, and other suitable properties are large relative to the length scales of the system); however, the flow path can alternatively be unidirectional, bi-directional, or have any other suitable characteristic(s).

Optionally, the solid supports can be washed (e.g., with buffer) to remove unbound molecules. This can occur, if ever, either before or after the solid supports from different samples are combined and/or before or after the solid supports have been introduced into wells of the array. In some embodiments, the solid supports are delivered to the wells in an ethanol-based solution. Once the solid supports are situated in the wells, the ethanol is allowed to dry leaving the solid supports with the bound targets in the wells.

Optionally, the solid support can be trapped inside the well. In some embodiments, a surrounding hydrogel matrix in sol form or in powdered suspension is flowed together with the solid support into the well, then converted to solid form once the solid support is in the well. In one embodiment a slurry of smaller beads is loaded together with the solid support blocking solid support movement post loading. In one embodiment a semi-permeable membrane is placed onto the wells after solid support loading. As discussed in more detail below, the wells can include a functionalized surface allowing for binding of target molecules from the solid support to the well surface.

If the target molecules are RNA, one can perform reverse transcription (RT) to form a first strand cDNA by introduction of a reverse transcriptase and appropriate reagents either before or after the solid supports from different samples are combined and before or after the solid supports are introduced into the wells of the array. Of in the case where the solid supports from different samples are not combined into a mixture, RT can be performed before or after the solid supports are introduced into the wells of the array.

In some embodiments, the wells of the array are sized such that the wells allow for one but only one solid support in a well. The solid supports are typically spherical (e.g., beads). However, in some embodiments, the size of the wells can be large enough to accept up to 2, 3, 4, 5, 6, 7, 8, 9, or 10 solid supports per well. The wells of the array can be a combination of wells of different depths such that no more than a quantum (0, 1, 2, 3, 4, 5, etc.) number of beads of the same size can be accommodated in the microwells and the location for each type of microwell of a certain depth is pre-determined Exemplary array of wells and well descriptions can be found for example in U.S. Pat. Nos. 9,103,754 and 10,391, 493. The array of wells (set of microwells, microwells, wells) functions to capture the solid supports, optionally in addressable, known locations. As such, the array of wells is preferably configured to facilitate solid support capture in at least one of a single-solid support format or optionally in small groups of solid supports as noted above.

The array of wells is preferably defined at the upper broad surface of a substrate, each well in the array of wells including a base surface defined within the substrate and proximal a second side (e.g., lower broad surface), an open surface directly opposing the base surface and proximal the upper broad surface, and a set of walls extending between the base surface and the open surface defining the well cavity of the well.

The array of wells can be defined at an active region of the substrate, wherein the active region can be any suitable area (e.g., 1 square inch, 10 cm, 2 square inch, 3 square inch, 4 square inch, etc.) of the substrate. Preferably, the active region (and the array of wells) of the substrate is accessible by other components of a system 100, including an imaging subsystem, fluid delivery module, thermal control module, and/or extraction module, in order to perform isolation, processing, and analysis of solid supports and captured target molecules as described herein. The array of wells 120 can include any suitable number of wells (e.g., on the scale of 100, 1,000, 10,000 wells, 50,000 wells, 100,000 wells, 1 million wells, 2 million wells, 3 million wells, 4 million wells, 5 million wells, 6 million wells, 7 million wells, 9 million wells, 10 million wells, 50 million wells, etc.). In preferred variations, the array of wells includes at least 250,000 wells. In a specific example, the array of wells includes approximately 1 million wells. However, the array of wells can be configured in any other suitable manner.

The open surface is preferably an opening in the substrate that provides access to the base surface of a well, and is configured to receive the solid support from a direction perpendicular to the upper broad surface of the substrate. As such, the open surface can have a characteristic dimension (e.g., width, diameter, circumference, etc.) that is larger than, smaller than, or equal to that of the base surface. In an example, the dimension of either the base surface or the open surface can range between 20 to 100 micrometers, and the height of the well cavity can range between 20 to 200 micrometers. In another variation, the characteristic dimension of the base surface and/or the open surface can range between 20 to 100 micrometers, and the height of the well cavity can range between 10 to 200 micrometers. However, in other variations, any dimension of the wells within the array of wells, including well cavity height and well cavity width, can be any value between 0.5 microns to 50 microns, and can optionally be selected based on the assay to be performed by the system and/or the dimensions of the solid supports. The open area of the array of wells (i.e., the sum total area of the open surface of each well in the set of wells) is preferably greater than 50% of the total area of the region of the substrate at which the wells are defined; more preferably, the open area is greater than 80% of the total area. However the open area can be any suitable fractional area or percentage of the total area of the substrate.

The open surfaces of each well are preferably aligned flush with the upper surface of the substrate (e.g., at a surface plane), but can alternatively be slightly recessed within the substrate or otherwise configured. Preferably, the open surfaces of the wells of the array of wells are aligned with a surface plane of the substrate, wherein the horizontal axes of the open surfaces are coaxial with the surface plane. In an example, the surface plane can be a plane with a lateral face parallel to the upper broad surface of the substrate, and defined at the intersection of the upper broad surface of the substrate and a region of space superior the upper broad surface of the substrate. In a specific example, the surface plane is a spatial boundary arranged between the upper broad surface of the substrate and a lower region of a fluid reservoir located superior the array of wells, and defined at the interface between the open surfaces of the array of wells and a fluid path within the fluid reservoir. In some embodiments, solid supports that are received into a well below the surface plane are not accessible by fluid flow at the open surface of the well, and are thus considered fully retained by the well cavity of the well, while solid supports traversing the surface plane or remain above the surface plane are accessible by fluid flow and are transmitted downstream of the fluid path, and are thus considered partially and/or non-retained by the well cavity. However, the surface plane can additionally and or alternatively be arranged with respect to any dimension of the substrate and/or the array of wells. Furthermore, the open surfaces of each well can be positioned with respect to any region of the substrate, fluid reservoir, and/or fluid path.

In preferred variations, the open surfaces of each well are directly fluidly coupled to a fluid path directly above and laterally superior to the array of wells. To enhance fluid flow across the open surfaces of the array of wells, the open surfaces of each well can optionally include a coating (e.g., hydrophobic, hydrophilic, electrostatic material, chemoattractive, etc.) or physical features (e.g., texturized, notched, ridged, etc.). Furthermore, the open surfaces of each well can optionally include passive or active retention features to retain and hold a single or small number of solid supports (e.g., physically or chemically triggered to increase or decrease open surface of well when well cavity is occupied). In one example wherein the open surface has a characteristic dimension smaller than that of the base surface, a well can have a lip that forms a boundary of the open surface in order to provide a characteristic dimension that is smaller than that of the base surface. The lip can be planar or non-planar, and can further facilitate retention of a single cell or a single cluster of cells at the well. Variations of the open surfaces of each well, which can define any geometry for receiving a cell and/or particle into the well cavity, including a circular opening, rectangular opening, hexagonal opening, or any other suitable shape are possible. The open surface can, however, include any other suitable feature that facilitates fluid flow or solid support reception from the well of the array of wells.

The base surface is preferably parallel to, symmetrical to, and directly opposing the open surface; however, in some variations, the base surface can alternatively be non-parallel to, non-symmetrical to, and/or offset from the open surface. Similar to the upper broad surface of the substrate, the base surface can be a planar surface or a non-planar surface, and in variations of the base surface having a non-planar surface, the non-planar surface can include convex and/or concave portions having any suitable geometric characteristic. Additionally or alternatively, the base surface can be any one or more of: textured (e.g., to facilitate desired fluid flow behavior, to attract or repel a given particle type, etc.), characterized by a desired porosity, characterized by a desired surface treatment, characterized by immobilized particles or biochemical moieties, and characterized by any other suitable feature that facilitates cell reception and/or retention in any other suitable manner. Though in some variations, the base surface is closed such that there is no fluid flow through from the open surface of the chamber through the bottom surface of the chamber, the base surface can be alternatively configured to include one or more fluid channels to allow egress of particles with characteristic dimensions less than the target cell in order to exit the well cavity. However, the base surface can be otherwise configured in any other suitable manner.

In relation to the base surface and the open surface, each well preferably has at least one wall (e.g., a set of walls) extending between the base surface and the open surface. In a variation, the walls of each well at least partially physically and fluidly separates an individual well from at least one other adjacent well, defines a depth, width, and/or cross-sectional dimensions of the well, and are preferably perpendicular to a plane defined by the horizontal axis of the open surface. Preferably, the wall thickness of the walls is between 4-5 micrometers, but can be any dimension less than 10 micrometers. The wall can extend vertically from a plane defined by the open surface to the base surface to define the well cavity; as such, in some variations, a well cavity of each well in the array of wells can be prismatic (e.g., cylindrical prismatic, hexagonal prismatic, polygonal prismatic, non-polygonal prismatic, etc.). In a specific example, the well cavity of each well defines a hexagonal prism. However, the wall can extend between the open surface and the base surface in any other suitable manner in other variations (e.g., curved walls, straight walls, bent walls, etc.). For instance, the wall can gradually reduce a characteristic dimension (e.g., diameter, horizontal cross section, vertical cross section) of the well from the open surface to the base surface (e.g., by forming discrete steps, by gradually adjusting the characteristic dimension in a linear or a non-linear manner with any suitable slope, etc.). However, in some variations, a well may not have a well-defined wall perpendicular to a plane defined by the open surface (e.g., the base surface may extend in some manner directly to the open surface without forming a wall perpendicular to the open surface). In examples, the base surface and the open surface can be separated, with or without a wall, by a distance (e.g., height of a well cavity) of between 0.5 microns to 50 microns (e.g., approximately 25 microns or approximately 40 microns). However, the wells of the array of wells can be configured with any other physical characteristic and/or dimension, in order to perform the isolation, processing, and analysis steps described in method. In some embodiments, a method can include selecting an array of wells with specific dimensions, numerosity, geometry, spatial arrangement and/or any other suitable characteristic, according to the dimensions of target solid supports desired to be captured and other parameters required to perform a specific assay using a system, e.g., as described herein. Additionally or alternatively, the set of walls can include a set of channels that fluidly couple each well to at least one adjacent well in the array of wells. In such variations, the channel(s) of a set of channels can be defined within a region of the substrate between adjacent wells, or can be defined by overlapping portions of adjacent wells. In a specific example, a channel can have a characteristic dimension of 5 microns, and in variations of the specific example, a channel can have a characteristic dimension ranging from 0.5 microns to 75 microns.

The walls of the array of wells are preferably constructed from the same material as that of the substrate (as described in a previous section), but can alternatively be constructed of any other suitable material to confer desired physical or chemical properties to the well cavities of the array of wells. For example, the walls can be configured to be non-permeable or semipermeable to various particles or fluids in solution that has entered the well cavities, and additionally or alternatively configured to be permanently or non-permanently rigid, flexible, or shape-changing (e.g., ability to expand open or collapse closed) to control cell and/or particle entry into the well.

The internal surfaces of the well cavity of each well in the array of wells (e.g., the sidewalls of the walls facing the interior of the well cavity can optionally be configured to interact with the contents retained within the well cavity (e.g., a captured solid support, biological material, non-biological material, non-cell particles, cell-particle pairs, etc.). To permit such interaction, the internal surfaces can include a functional feature (physical or chemical) or surface-bound moiety on all sidewalls of the well cavity, but can alternatively be localized to any suitable portion or specific region of the well cavity (e.g., at the base surface, proximal the open surface, along the sidewalls, etc.). In a first variation, the internal surfaces include a functional surface coating configured to bind to nucleic acid content that has been released from a captured solid support. The functional surface coating can be of synthetic, animal derived, human derived, or plant derived proteins. In an example, the functional surface coating permits biotinylated surface chemistry (e.g., biotin-streptavidin linkers) to bind to a probe including a functional linker. However, the functional surface coating of the internal surface of a well can be configured to bind to any contents retained within the well cavity in any other suitable manner. In a second variation, the functional surface coatings are configured to physically retain and/or manipulate the captured content, such as orienting a captured particle in a particular direction for downstream analysis (e.g., optical imaging). In an example, the functional surface coatings include a polymer or protein providing a sticky layer to adhere to a region of the captured target cell (e.g., polymer adhesive, catechol-polystyrene, poly-D-lysine, fibronectin, collagen, vitronectin, etc.). In another example, the functional surface coating includes a polymer or protein that attracts a cell towards the open surface of the well, or is a semi-permanent barrier at the open surface of the well to control entrance of particles into the well. In a third variation, the internal surfaces of the well are configured to add a chemical agent (e.g., a drug interacting with the cell, an agent that controls pH of the solution within the well, an agent that controls density of fluid within the well, etc.), biochemical agent (e.g., a fluorescent marker, antibodies, etc.), and/or a process reagent (e.g., a lysis buffer contained in a timed-released delivery vehicle/microsphere, etc.), in order to perform downstream assays and analysis of the captured cells. In a fourth variation, the internal surfaces of the well can include physical features to increase, decrease, or vary the surface area (e.g., ridges, protrusions, pores, indentations within the well cavity). Furthermore, the physical features can include functionalized microparticles that have been immobilized within the well, reflective components to enhance optical access and optical interrogation of contents retained within the well, and/or magnetic elements to manipulate the position of the cell or particle within the well.

While every well in the array of wells can be substantially identical, the array of wells can alternatively include wells that are non-identical to each other by any suitable feature (e.g., size, morphological feature, mechanical feature, surface coating feature, thermal conductivity feature, electrical conductivity feature, etc.). As such, some variations of the system can be configured to capture at least one of multiple particle types and particles in multiple types of formats, in addressable locations, for processing and analysis.

In variations including subsets of wells, the subsets can be separated from one another. In a first variation, each subset can be separated from other subsets by a portion of the substrate in which no wells are defined (e.g., a flat region of the broad surface). In a second variation, the subsets can be fluidically-isolated regions of a contiguous arrangement of wells, in which none of the wells of a particular subset are fluidly coupled to a well of another subset. Separate addressable subsets can be used in one embodiment to receive solid supports from different samples (e.g., where solid supports from different samples have been mixed and are tracked via their location in the array). In some embodiments, the subsets can be separated by vertical splash shields that prevent contamination of different subsets upon application of fluids from above the substrate. In a specific example, the substrate defines distinct subsets of the array of wells, e.g., arranged in a two-by-six grid, that are separated from adjacent subsets by flat region of the broad surface, with a uniform spacing (e.g., 1 mm, 100 microns, 3 mm, etc.) between array edges. The subsets of wells can be further divided into groups (e.g., groups of seven wells within a subset of 20,000 wells of a 250,000 well set of wells), and any suitable interconnectivity between wells (e.g., among subsets, between groups, etc.) can be provided by the set of channels of each well. Such configurations may permit efficient bead capture (e.g., by a group including seven interconnected wells) by groups of wells, while allowing the set of wells to be exposed to multiple distinct samples (e.g., one sample per subset of the set of wells). In an example, wells can be approximately 30 microns in diameter, 30 microns deep, and wall thicknesses of 4-5 microns (e.g., which provides more efficient cell capture). However, in related variations, the array of wells can alternatively be subdivided and/or interconnected in any suitable manner. The subsets and/or groups of wells can be arranged in any suitable manner. For example, the subsets can be arranged in a rectilinear fashion (e.g., a grid layout of well subsets) and the groups can be arranged in a packed configuration (e.g., hexagonal close-packed, square lattice, etc.), and vice versa; the arrangement of the groups and subsets are preferably independent of one another, but can alternatively be based on one another (e.g., the subsets are arranged in a rectilinear fashion because the groups are arranged in a rectilinear fashion). Furthermore, each substrate 110 of the system 100 can have a single array of wells, or can have multiple subsets of wells defined at the substrate in any suitable manner (e.g., in a radial configuration, in a rectangular configuration, in a linear configuration, in a curvilinear configuration, in a random configuration, etc.).

In a specific example of the array of wells, an array of wells can be embossed into a plastic (e.g., material COP480R) using a photolithographic etching process. A fluid reservoir can then be provided (e.g., glued or otherwise attached) around the active region containing the array of wells that allows a relatively large liquid sample to be placed during use (e.g., 0.5 mL to 5 mL). In some embodiments, two microchannels can be included that serve as inlet and outlet to the reservoir fluidly coupled to the array of wells at the active region. A solid support-containing sample, (e.g., up to 1 ml in volume), can be dispensed into the fluid reservoir formed by the recessed region of a first plate of a fluid delivery model surrounding the active region of the substrate. Solid supports present in the sample will settle down (e.g., gravity-induced entry) over time through the fluid layer in the reservoir, and into the interior of the well cavity through the open surfaces of the wells. In specific applications, the settling time depends on the size of the solid supports. Once the solid supports enter the well cavities, such that the entire volume of the solid supports is fully contained within the well cavity (e.g., fully retained, descends below the surface plane, descends below the open surface of the well), they are captured in single solid support format (or as discussed herein in some cases, in group of fewer than 10, fewer than 5, etc.). Because the walls in between each of the wells in the array of wells are thin (e.g., less than 10 microns thick, less than 5 microns thick, etc.), most of the solid supports tend to settle inside and are fully retained within the well as opposed to on top of or partially retained by the wells. In some embodiments, the depth of the well is no more than 1.2, 1.3, 1.4, 1.5, 1.6, or 1.7 times the diameter of the solid support.

Furthermore, the array of wells is preferably arranged in a packed array, but can alternatively be arranged in any other suitable manner. In one example, the array of wells can be arranged in a hexagonal close-packed array. In another example, the array of wells can be arranged in a rectangular array. In another example, the array of wells can be arranged in any suitable irregular or non-uniform manner, for instance, to facilitate fluid flow from one portion of the array of wells to another portion of the array of wells. The array of wells can alternatively be arranged with any suitable spacing between wells (e.g., in a packed or a non-packed configuration), and in any other suitable manner.

In a specific example configuration of the set of wells, the array of wells is arranged in a hexagonal close-packed configuration, wherein each well of the array of wells includes a hexagonal open surface aligned with the broad surface (e.g., surface plane) of the substrate. Furthermore, each well includes a hexagonal footprint at the base surface opposing the hexagonal open surface. In some embodiments, each well of the array of wells has a well cavity that forming a hexagonal prism, (e.g., including a set of walls approximately 5 micron in thickness, a height of approximately 25, or 40 or 20-30 micrometers, and a characteristic width of approximately 25 (e.g., 20-30) micrometers), and in some embodiments the solid support is a bead having diameter of 18-22, e.g., 20 microns. However, the array of wells can be configured in any other suitable manner.

In some variations of the system, one or more wells of the array of wells can further include any other suitable element that facilitates stimulation and/or detection of a parameter (e.g., a presence or absence of a detected target molecule parameter) at the well(s) of the array of wells. In one example, one or more wells of the array of wells of the array of wells can include an electrode embedded in the substrate at a surface of the well in order to facilitate detection of bioelectrical signals from contents of the well, and/or to facilitate stimulation of the contents of the well. In variations of the example, the electrode can be embedded with an exposed portion at least one of the base surface and a wall of the well. In other examples, the well(s) can be coupled to channels that facilitate delivery of process reagents to a cell/cell cluster at a well, or facilitate extraction of contents of a well (e.g., processed intracellular contents) from the well. The system can, however, include any other suitable element that facilitates processing and/or analysis of cells in at least one of single-cell format and single cluster format.

As noted above, in some embodiments, the wells in the array can vary in their size (e.g., volume, opening size, capacity to hold number of solid supports. Alternatively, all of the wells can be of uniform size. In some embodiments in which the wells have uniform size, different solid supports can vary in size and can vary in a separate characteristic (for example but not limited to, color). In either case in which well size or solid support size vary, a situation can occur in which more than one solid support can accumulate in the same well. Because more than one molecule can bind to a single solid support and multiple supports with bound targets can accumulate in a single well in these embodiments, the relative signal intensity from each well (e.g., proportional to the number of solid supports in each well) can vary. The difference in signal intensities between wells together with the presence or absence of signal in each well can be used to measure the concentration of target molecules in a sample. In these embodiments, the number of solid supports is lower than the number to saturate all capacity of the wells, the accumulation of more than one solid support in a well. See, for example, Si et al., *Sensors and Actuators B: Chemical*, Volume 318, 1 Sep. 2020 and its discussion of such determinations in other contexts.

As noted above, in some embodiments, the wells in the array can include an affinity agent that binds to target molecules. This allows for elution of the target molecules from the capture molecules on the solid supports, allowing for additional manipulation of the target molecules as desired. For example, one can perform a wash of the well to remove components of the solution in the well while not displacing the target molecules, which remain bound by the affinity agent. In one embodiment the capture agent is a capture oligonucleotide and the affinity agent is a different capture oligonucleotide with a higher Tm than the capture oligonucleotide on the solid support. In one embodiment the affinity agent is immobilized to the walls of the well, solid supports bound to the walls of the well and/or a hydrogel matrix solidified in the well. In one embodiment, during amplification, the target molecules do not bind to the affinity agent due to the high temperatures during thermocycling or the affinity agent is in solution, such that when amplification is complete the target molecules bind to the affinity agent due to a reduction of temperature and/or the affinity agent is fixed in the well. For example an acrydite oligo is used as a primer during PCR amplification that occurs in polyacrylamide solution matrix in the well. Upon completion of amplification, polyacrylamide crosslinking is initiated. Lambda exonuclease can be used to degrade the unprotected non-acrydite strand. The single stranded amplicon products can then be probed with successive rounds of fluorescent molecular beacons to detect sequence variation.

Following introduction of the solid supports into the wells of the array, the wells can be covered to prevent evaporation, diffusion into neighboring wells, and/or to retain the solid supports. Any sort of cover can be used. In some embodiments, the cover is solid, and in some embodiments translucent or clear to allow for detection of signal within the wells. In another embodiment, the cover is a layer of oil placed across the top of the wells. In another example, the cover can be a layer of gel. As exemplary gel is an acrylamide gel but other types of gel can also be used. In another example, the cover could be an elastomeric layer present on the bottom of the lid used to cover the wells from the top and mechanically mated to the top surface of all the wells. In another example, a bead slurry of beads smaller than the solid support with the capture moiety can be added to the wells to embed the larger solid support in a matrix of smaller beads.

In some embodiments, a gel layer can be delivered to each well in the form of a bead that is subsequently melted, e.g., using heat, or dissolved, e.g., by disruption of the crosslinks that hold the gel bead structure together. The beads supplying the gel layer can in some embodiments be the beads that are linked to the capture molecules. In other embodiments, the beads supplying the gel layer are separate beads.

In embodiments in which target molecules are nucleic acids, the nucleic acids can be amplified in the wells (optionally under the cover as described above) and then the amplified target nucleic acids can be detected, preferably such that the presence or absence of amplified product can be detected optically. Amplification can be performed under isothermal or thermocyclic conditions. For example, the amplification can compromise reverse transcription (RT), RT-PCR, Loop-mediated isothermal amplification (LAMP) (which is isothermal), RT-LAMP, or bridge amplification.

Optionally, the cover can be removed at some point in the method prior to detection. For example, where further manipulation of the contents of the wells is desired before detection, additional reagents for detection can be added to the wells (e.g., by flowing a solution comprising the reagents under or over the wells) after the cover is removed Detection of the target molecule, which may be amplified, can be performed in any way useful to generate a detectable signal. Preferably the signal can be detected optically, for example such that an automated scanner can detect the presence, absence or quantity of signal in each well. Signal can increase upon presence of the target molecule or in other embodiments signal can decrease (e.g., in the case of quenching of signal in the presence of the target molecule).

In some embodiments, the wells comprise one or more optically detectable agents such as a fluorescent agent, phosphorescent agent, chemiluminescent agent, etc. Numerous agents (e.g., dyes, probes, or indicators) are known in the art and can be used. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. In some embodiments, the agent is a fluorophore. A vast array of fluorophores are reported in the literature and many are readily available from commercial suppliers to the biotechnology industry. Literature sources for fluorophores include Cardullo et al., *Proc. Natl. Acad Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995). Non-limiting examples of fluorophores include cyanines, fluoresceins (e.g., 5'-carboxyfluorescein (FAM), Oregon Green, and Alexa 488), HEX, rhodamines (e.g., N,N,N'N'-tetramethyl-6-carboxyrhodamine (TAMRA), tetramethyl rhodamine, and tetramethyl rhodamine isothiocyanate (TRITC)), eosin, coumarins, pyrenes, tetrapyrroles, arylmethines, oxazines, polymer dots, and quantum dots.

In some embodiments, the detectable agent is an intercalating agent. Intercalating agents produce a signal when intercalated in double stranded nucleic acids. Exemplary intercalating agents include e.g., 9-aminoacridine, ethidium bromide, a phenanthridine dye, EvaGreen, PICO GREEN (P-7581, Molecular Probes), EB (E-8751, Sigma), propidium iodide (P-4170, Sigma), Acridine orange (A-6014, Sigma), thiazole orange, oxazole yellow, 7-aminoactinomycin D (A-1310, Molecular Probes), cyanine dyes (e.g., TOTO, YOYO, BOBO, and POPO), SYTO, SYBR Green I (U.S. Pat. No. 5,436,134: N',N'-dimethyl-N-[4-[(E)-(3-methyl-1,3-benzothiazol-2-ylidene)methyl]-1-phenylquinolin-1-ium-2-yl]-N-propylpropane-1,3-diamine), SYBR Green II (U.S. Pat. No. 5,658,751), SYBR DX, OliGreen, CyQuant GR, SYTOX Green, SYTO9, SYTO10, SYTO17, SYBR14, FUN-1, DEAD Red, Hexidium Iodide, ethidium bromide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, LDS 751 (U.S. Pat. No. 6,210,885), and the dyes described in dyes described in Georghiou, Photochemistry and Photobiology, 26:59-68, Pergamon Press (1977); Kubota, et al., Biophys. Chem., 6:279-284 (1977); Genest, et al., Nuc. Ac. Res., 13:2603-2615 (1985); Asseline, EMBO J., 3: 795-800 (1984); Richardson, et. al., U.S. Pat. No. 4,257,774; and Letsinger, et. al., U.S. Pat. No. 4,547,569.

One method for detection of amplification products is the 5'-3' exonuclease "hydrolysis" PCR assay (also referred to as the TaqManm assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the TaqMan™ probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Thus, in some embodiments, the detectable agent is a molecular beacon oligonucleotide probe. The "beacon probe" method relies on the use of energy transfer. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched.

In some embodiments, the sample nucleic acids can be detected using the SHERLOCK method (Specific High Sensitivity Enzymatic Reporter UnLOCKing). This method provides an in vitro nucleic acid detection platform with high (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," Science, 356(6336):438-442 (2017) and US Patent Publication No. 20180340219.

In some embodiments, non-natural nucleotides that base pair and comprise quenchers and fluorescent reporter can be used. For example, step-down technology such as is available from Luminex under the name MultiCode® Technology. In this technology, site-specific interaction of the reporter-labeled first non-natural nucleotide with the quencher-labeled complementary non-natural nucleotide during amplification produces a decrease in fluorescence.

In some embodiments, the wells can be probed with multiple different probes, either simultaneously (where detectable signal from two or more probes are separately detectable) or by testing each in series, washing probes away from the wells in between probing with different probes.

Signal, or change in signal, in the wells can be detected as desired. For example, a detection system can be configured to image the array of wells and count the wells with a detectable target nucleic acid product and optionally the detectable characteristic of the solid support, so that the well signal can be linked to a particular sample. Accordingly, system can additionally include an imaging subsystem that functions to image the contents of the set of wells, and can further function to distinguish target objects (e.g., CTCs, labeled cells, microspheres) captured in the set of wells from other cells or objects in the sample introduced into the system. The imaging subsystem preferably includes a fluorescence microscope, but can additionally or alternatively include any suitable imaging mechanism (e.g., an optical microscope, a CCD camera, a CMOS camera, a photodiode array, a light emitting diode, reflectors, one or more processors, etc.). The fluorescence microscope is preferably operable (e.g., in an identification mode, a detection mode, etc.) to detect a fluorescence signal emitted from a target object one or more of the set of wells, and thereby identify that the well(s) contain(s) a target molecule. In a specific example, the imaging system (e.g., fluorescence imaging system) can be operable in a mode for providing real-time or near real-time fluorescence imaging of samples processed according to an assay. The imaging subsystem is preferably positioned beneath the substrate and oriented to image the contents of the set of wells through the transparent (or translucent) material of the substrate; alternatively, the imaging subsystem can be positioned above the substrate and oriented to image the contents of the set of wells unobstructed by the material of the substrate itself. However, the imaging subsystem can be otherwise positioned in any suitable manner. Optionally, the imaging subsystem can detect intensity of signal as well as the presence or absence of signal. Data processing can be used to normalize signal and for example to distinguish sample signal from background signal. The well array may also have a heating system integrated to heat the contents of the microwell to desired temperatures in a programmed manner for either isothermal incubations or rapid thermocycling and/or probe hydridizations and/or melting operations.

In some embodiments, the system comprises one or more computer processer configured to receive signal from the detection system. The signal from the detection subsystem can include, signal or signal intensity from detection of the target molecule, signal or signal intensity representing the distinguishable characteristic of the solid support, if present, and/or optionally the location (address) of the well in the array. The relative or absolute copy number of target molecule in the sample can be determined based on the number of wells having signal for the presence of the target molecule and optionally taking into consideration the intensity of the signal in embodiments in which more than one solid support can fit into a well. The total number of wells having a solid support from the sample can also be determined and used to calculate target molecule copy number in the sample.

In embodiments in which solid supports are distinguishable, the detection subsystem can also deliver to the computer processor(s) the sample origin of each solid support based on the distinguishing characteristic. Alternatively, or in addition, the detection subsystem can deliver to the computer processor(s) the location of each well for each signal detected, allowing for sorting of target molecule data by sample origin, thereby allowing for processing of multiple samples.

The processor can also calculate concentrations of target molecules based on intensity of signal caused by multiple solid supports within a single well, in embodiments where that option exists.

The computer processor can be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, can be included. Where the host computer is attached to a network, the connections can be provided via any suitable transport media (e.g., wired, optical, and/or wireless media) and any suitable communication protocol (e.g., TCP/IP); the host computer can include suitable networking hardware (e.g., modem, Ethernet card, WiFi card). The host computer can implement any of a variety of operating systems, including UNIX, Linux, Microsoft Windows, MacOS, or any other operating system.

Computer code for implementing aspects of the present invention can be written in a variety of languages, including PERL, C, C++, Java, JavaScript, VBScript, AWK, or any other scripting or programming language that can be executed on the host computer or that can be compiled to execute on the host computer. Code can also be written or distributed in low level languages such as assembler languages or machine languages.

Scripts or programs incorporating various features of the present invention can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

Figure 4:
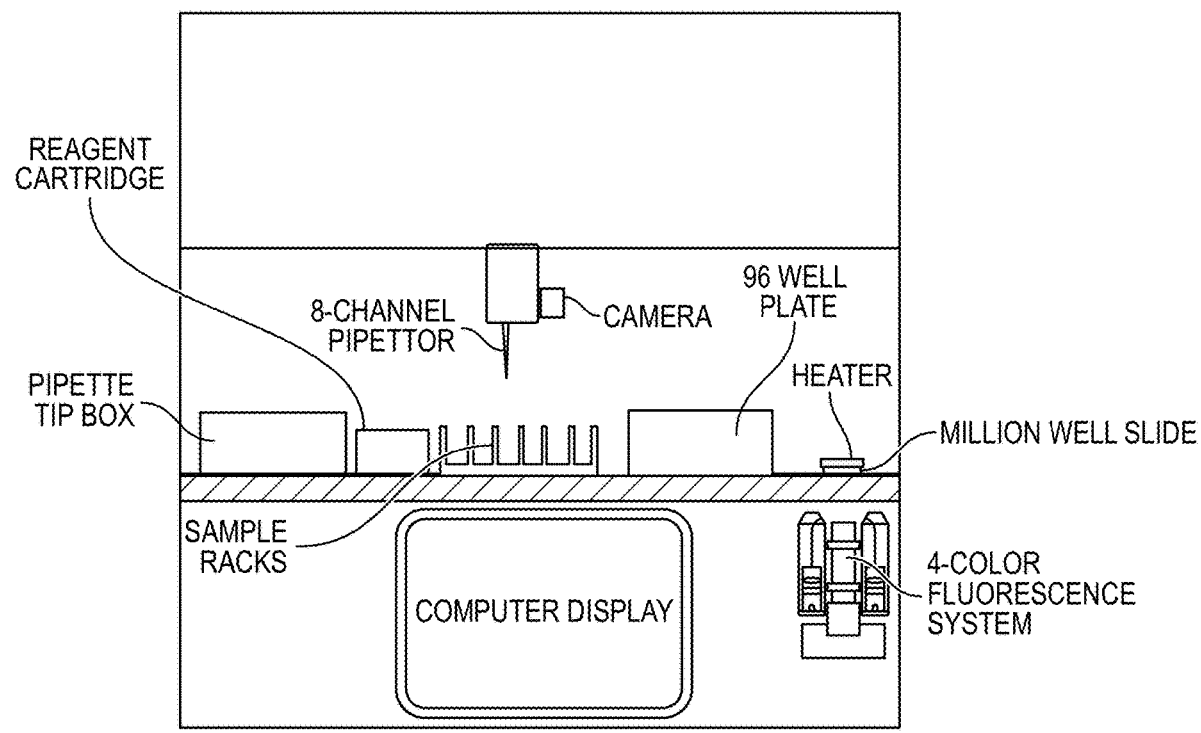
FIG. 4 depicts an exemplary system comprising 8-channel independent pipettor, a 96 well plate with pre-aliquoted lysis buffer containing RNA capture beads; beads color-coded for each sample, allowing for sample identification, a slide (array) with million microwells allowing minimum of 10,000 partitions per sample. An exemplary protocol can be: 10 minute lysis and binding followed by 20 minute real-time LAMP (or Fast PCR), and detection in wells wherein 96 Sample-to-Results occurs in 50 minutes. In some embodiments, new sets of samples can be loaded every 30 minutes allowing 1536 samples in 8 hours.

An exemplary system is depicted in FIG. 4. Subsystems of the system can include one or more of the following, for example:
- (a) Computer and a Display for the User Interface;
- (b) A xyz gantry system that can move a z-head across the deck to various liquid handling operations;
- (c) Z-head containing a multi (e.g., 8-channel) pipettor and a camera to read barcodes of various consumables and to provide feedback on the state of various consumables;
- (d) 4-color fluorescence detection system capable of uniform illumination of the microwell slide (array) and to detect fluorescence images of an area of the microwell slide with resolution of a fraction of the size of the microwells;
- (e) A heater that can thermocycle or provide isothermal heating to the microwell slide; and
- (f) A deck comprising the one or more consumables.

Exemplary consumables on the deck can include one or more of:
- a. A multi-well slide (array) that can have for example, $10^5$-$10^7$ or more wells, where beads from different samples are captured in microwells and real-time digital PCR (or other amplification reaction) is performed;
- b. A multi-well (e.g., a 96 or 384-well) plate where samples containing nucleic acids are lysed followed by binding of the nucleic acids to beads. The beads can optionally also be washed in the same 96 well plate to remove contaminants from the beads;
- c. A reagent cartridge that contains wash reagent, amplification and detection reagents and oil and tip to transfer amplification and detection reagent to the multi-well slide and tip to transfer oil to the multi-well slide;
- d. one or more pipette tip boxes containing tips for:
  - i. transfer of sample from sample tubes to 96 well plate; same tip can optionally be used for mixing and removing supernatant after beads have already bound nucleic acid or other target molecules from samples;
  - ii. wash beads to remove contaminants
  - iii. transfer beads to the multi-well slide
- e. sample racks
  - i. Sample racks allow strips of 8-well tubes containing samples to be loaded into the instrument. Each sample gets a unique barcode that links the clinical sample to the precise location of the sample in the Sample Rack. During the run set-up, the user marries the Sample ID with the Sample Tube ID.

Figure 5:
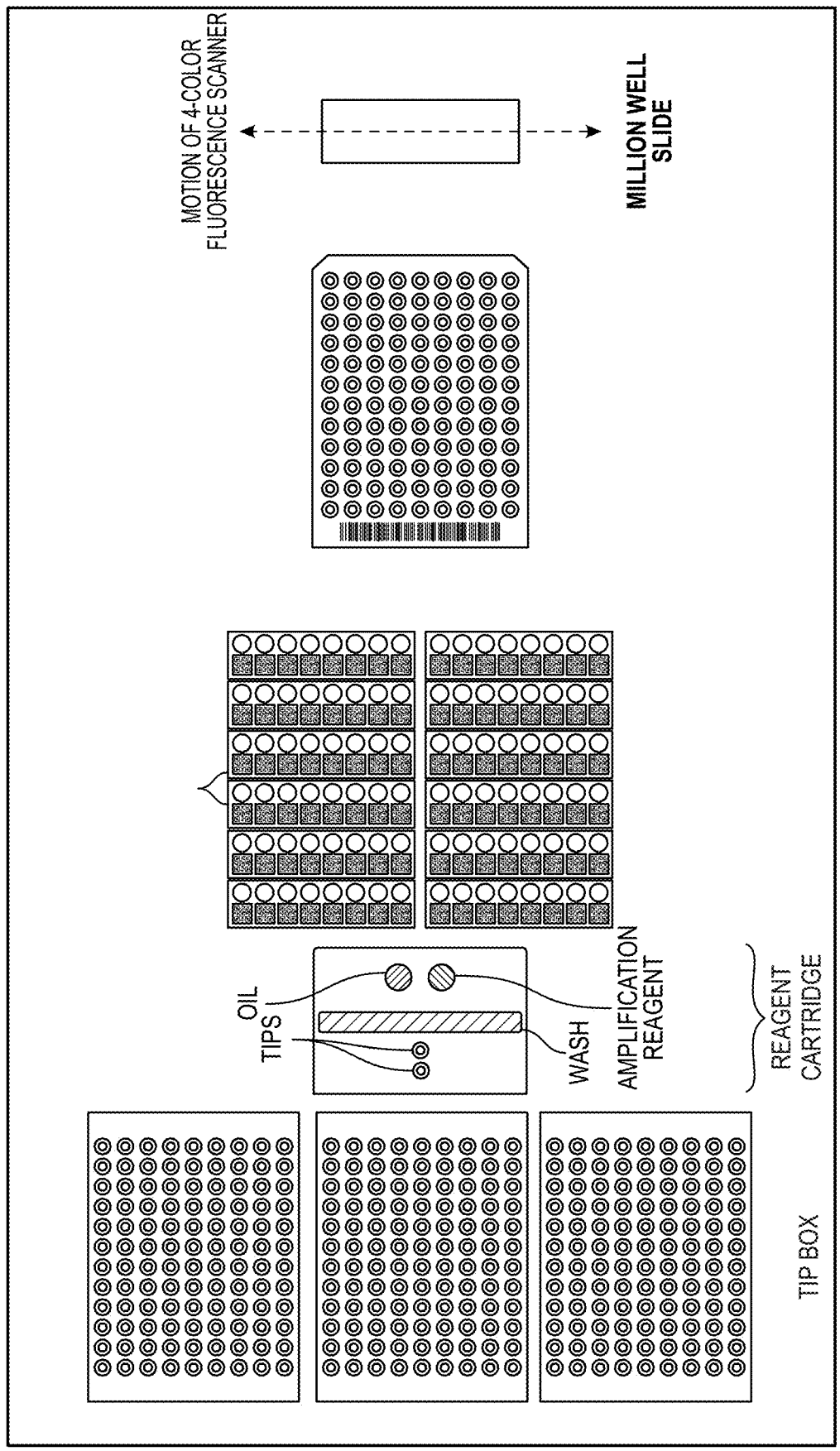
FIG. 5 depicts a landscape view of a system for practicing the methods described herein.
Figure 6:
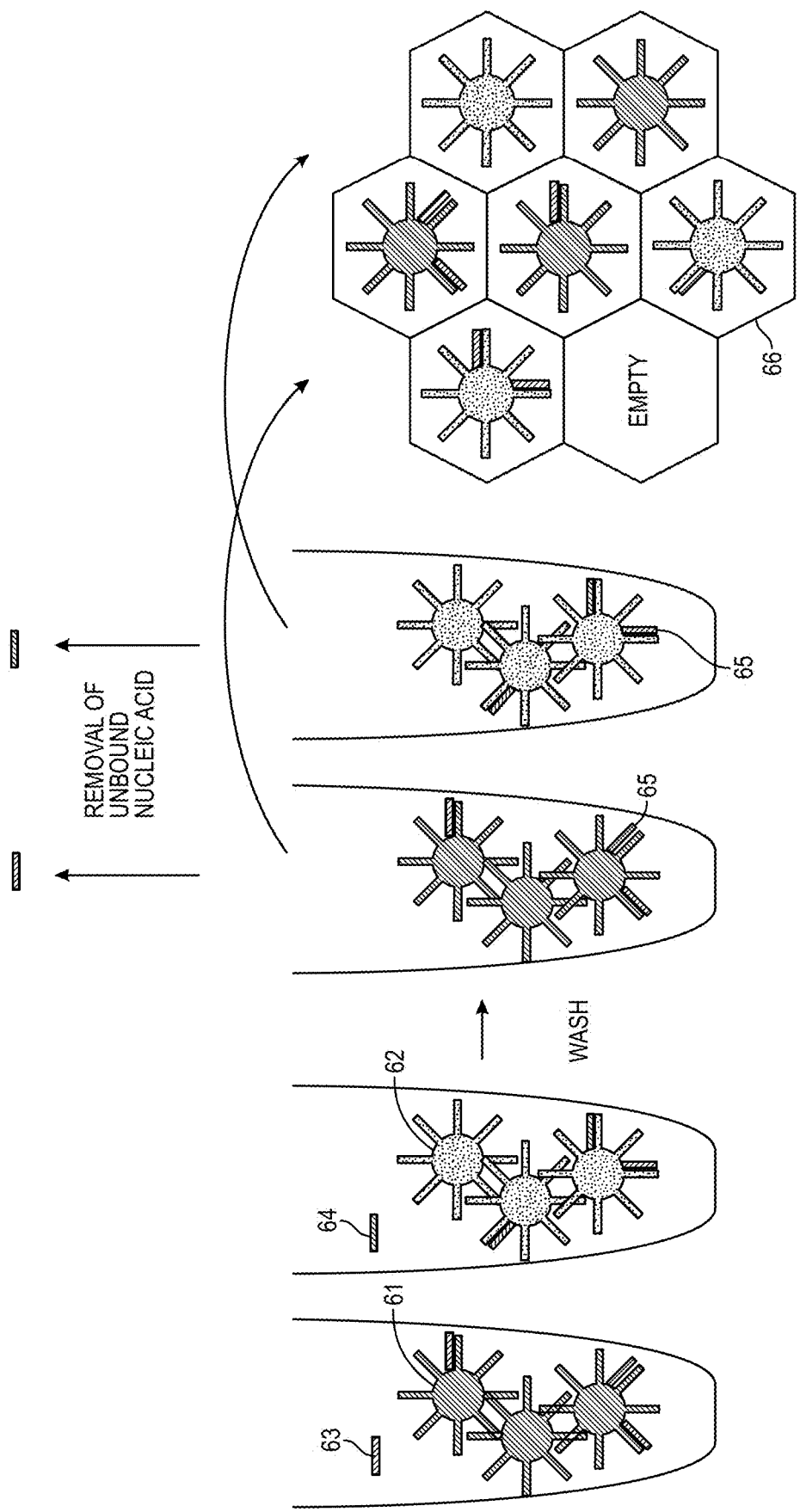
FIG. 6 depicts a workflow in which different color beads (61 and 62) are mixed with different samples (63 and 64), unbound components are removed and then the bound target molecules (65) are introduced into hexagonal wells (66).
Figure 7:
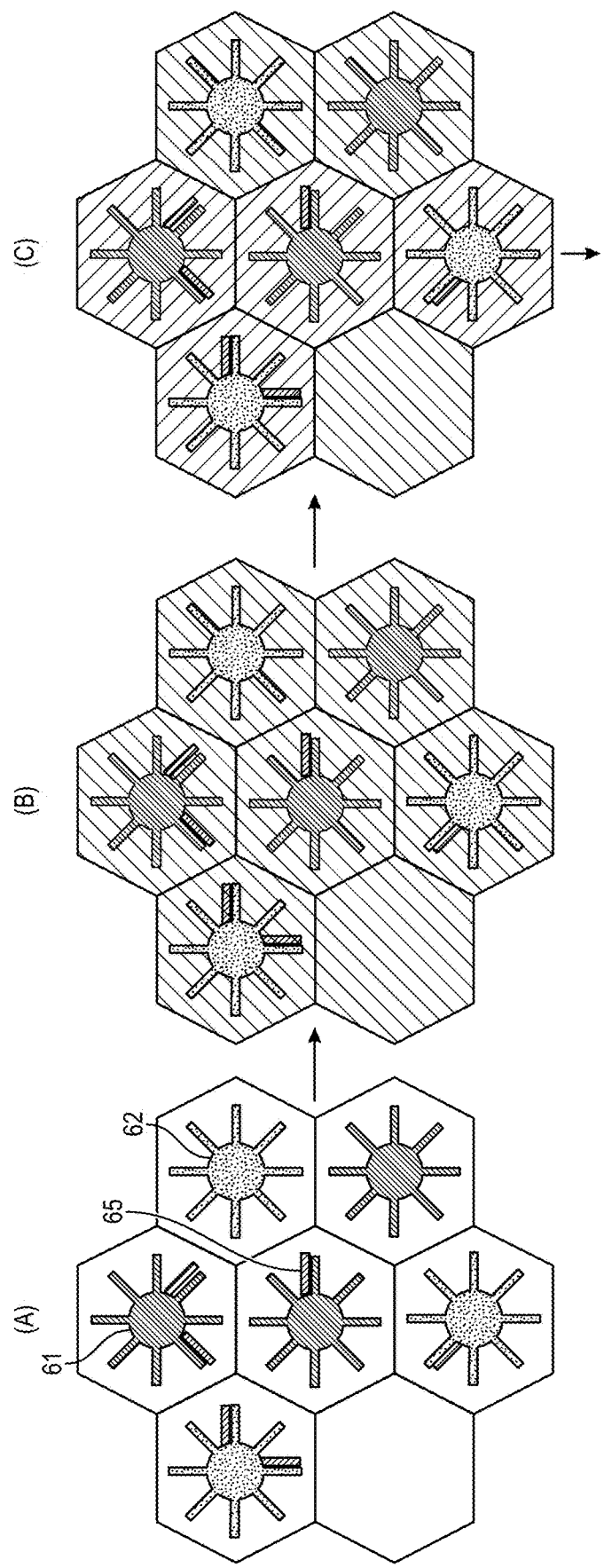
FIG. 7 depicts a continuation of the workflow from FIG. 6. Once colored beads (61 and 62) and bound target molecules (65) are introduced into the wells as depicted in (A), an oil cover layer (depicted as lines from lower left to upper right of wells) is introduced as depicted in (B) and the target nucleic acids are amplified. In (C), target signal (depicted as lines from lower right to upper left of wells) is detected as well as bead color.
Figure 8:
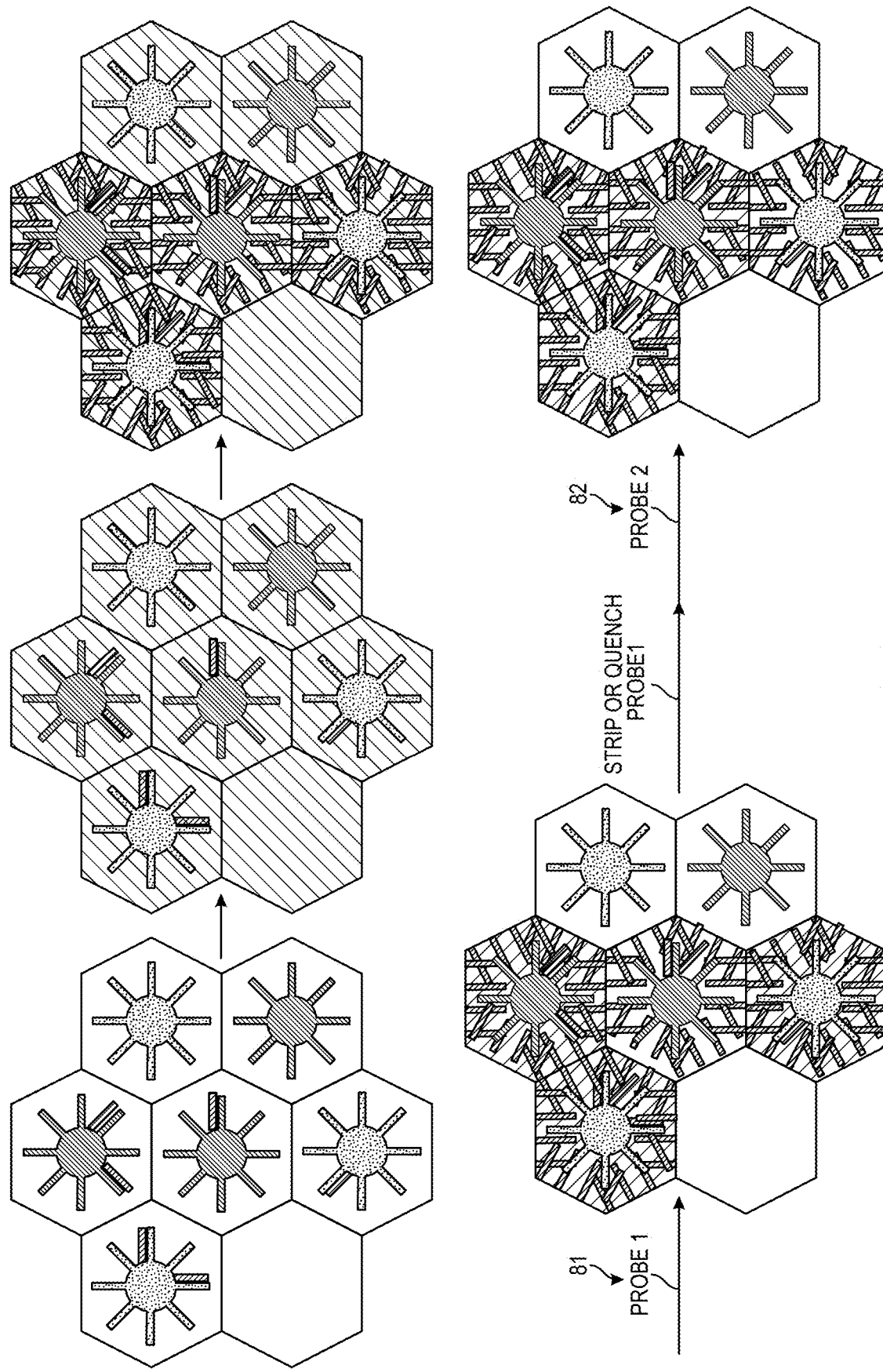
FIG. 8 depicts an embodiment in which a first probe (81) is used to detect a first target in the wells and then the first probe is washed away and a second probe (82) is used to detect a second target.

FIG. 5 shows the deck of the instrument showing various consumables used to process 96 clinical samples at the same time. Exemplary consumables can include one or more of:
- (a) Sample tubes;
- (b) A multi-well (e.g., 96 or 384-well) plate containing lysis reagents and beads for nucleic acid preparation and binding the nucleic acid or other target molecules to the beads;
- (c) A reagent cartridge, optionally containing one or more of a wash reagent, amplification reagent, oil and tips for loading reagents into the multi-well (array) slide;
- (d) A multi-well slide (array) that can have for example, $10^5$-$10^7$ or more wells, that performs digital real-time PCR of 96 samples (e.g., 10,000 beads/sample) simultaneously;
- (e) One or more tip Boxes A process can be performed on the instrument of FIG. 5, running 96 samples, as outlined below:
- (a) User loads clinical sample in sample strips. Each sample can have a unique barcode. Samples can be loaded in strips, for example, of 8. In the depicted embodiment, a maximum of 96 samples can be loaded in the instrument.
- (b) User loads other consumables, e.g.:
  - a. Multi-well slide (array).
  - b. 96 well plate, optionally containing one or more of lysis reagents and beads.
  - c. A reagent cartridge
  - d. One or more tip boxes
- (c) The xyz gantry moves the camera over various consumables, checks for barcodes and determines that the deck has all necessary consumables loaded to process all 96 samples.
- (d) The pipettor picks up tips from the tip box in groups of 8 and transfers samples (~100 µl) from the sample tube and dispenses it into tube 1-8 of the 96 well plate. The reagents are mixed causing the lysis and binding of nucleic acids to the beads.
- (e) The pipettor drops the tips in the tip box and continues the operation for the next samples until all samples are transferred to the 96 well plate to initiate lysis and binding.
- (f) Processed samples are given enough time to incubate. At the end of the incubation process, the beads in each sample settle by gravity to the bottom.
- (g) The supernatant is transferred to the sample tube.
- (h) Wash is added to each of the wells of the 96 well plate.
- (i) The beads are then transferred to the multi-well slide from the microwell. During this process, the lid of the multi-well slide is kept open such that the microwells are accessible from the top.
- (j) After all beads (e.g., 10,000 beads per sample) from 96 samples are dispensed in the multi-well slide, wait for a few minutes for the beads to settle into its microwells. The pipettor may be used to cause gentle agitation to promote all beads to find its microwell.
- (k) The hinged lid of the multiwall slide is closed using the pipettor using a lid opening/closing tool.
- (l) Amplification reagent is delivered into the multi-well slide from an inlet port allowing all microwells to receive amplification and detection reagent.
- (m) Oil is then dispensed into the inlet port of the multi-well slide to partition the microwells from each other.
- (n) A heater in engaged on top of the lid to perform thermal incubations as required for the amplification reaction.
- (o) At pre-determined time intervals, all the microwells are imaged in brightfield as well as fluorescence to monitor the progress of the amplification reaction using the 4-color fluorescence system.
- (p) Using the processor and a pre-determined algorithm, the number of beads for each sample is determined to be positive and results for each sample is then displayed in a quantitative manner.

Figure 9:
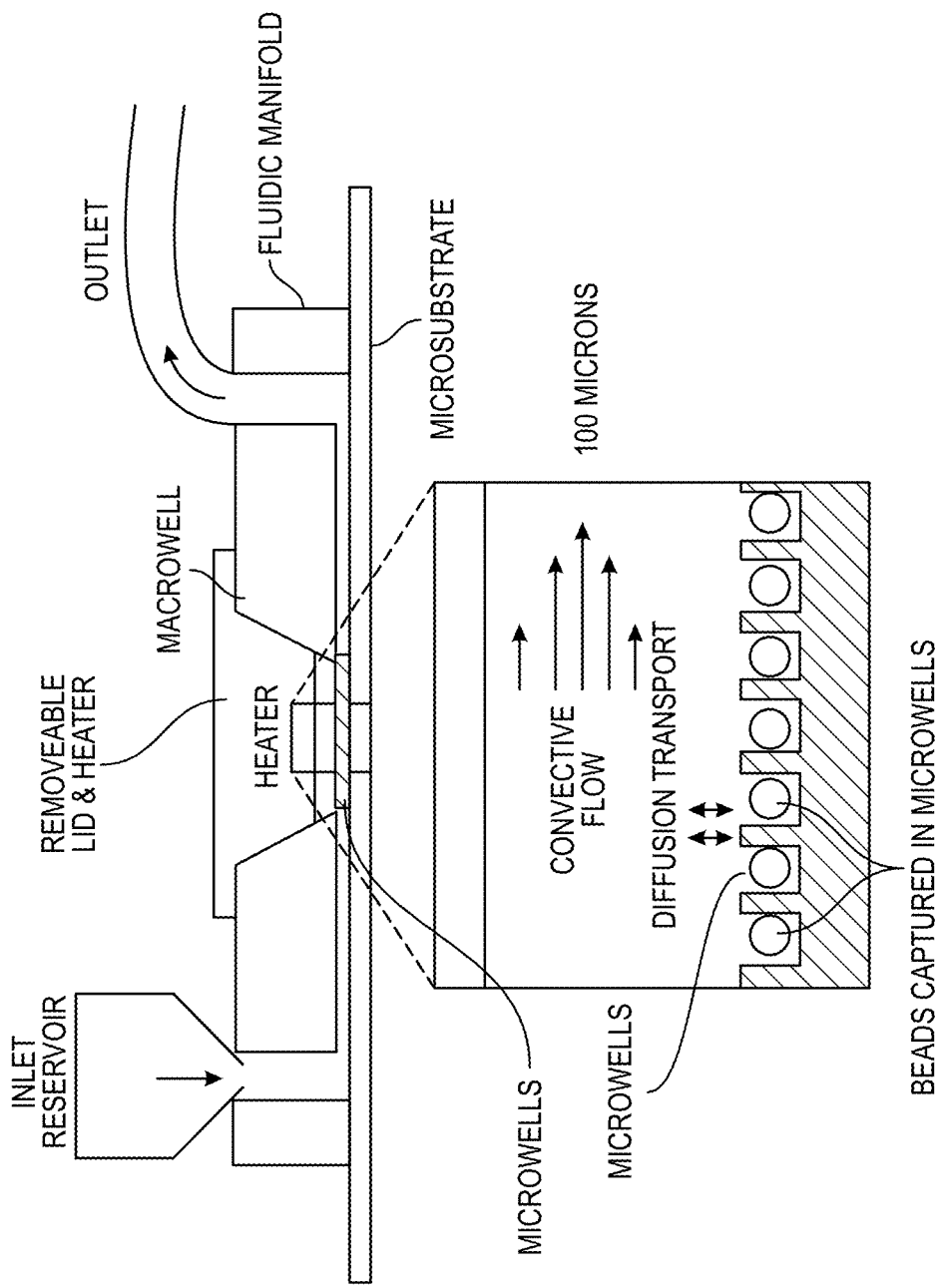
FIG. 9 depicts
Figure 10:
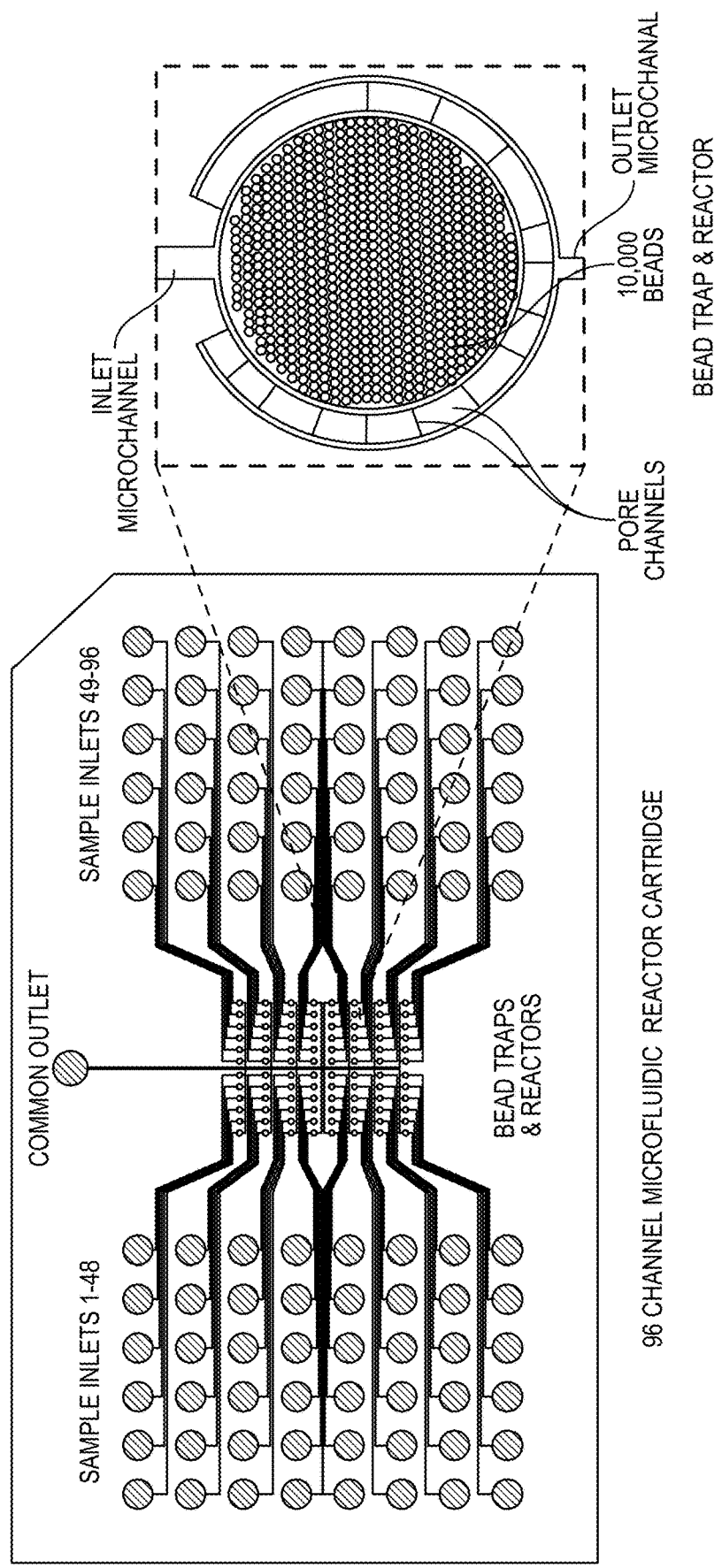
FIG. 10 depicts a 96-channel microfluidic reactor cartridge that can process 96 clinical samples through the entire process of target nucleic acid capture from clinical samples to amplification and detection in the same microfluidic reactor. Each sample lane has a bead reactor as shown in the right panel above. The reactor is capable of housing multiple beads (e.g., 10,000 beads) in a monolayer format. The beads are introduced from the inlet microchannel that is connected to the Sample Inlet port. Multiple pore channels smaller in diameter (for example, 15 micron pore channel for capturing 20 micron-sized beads) emanate from the bead reactor and then all combine into the outlet microchannel. The multiplexed cartridge houses multiple reactors where each sample has their own dedicated sample inlet ports (e.g., Sample Inlet 1-96) but they all have a single outlet port to share the same outlet reservoir that can be connected to a single vacuum source for flow of samples and reagents through the different reactors. Each of the reactors are mated with an individually controllable themocycling heater or a large combined thermocycling heater on one surface of the reactors. The reactors are also imaged by a fluorescence scanner to detect the presence of beads in the reactor and/or detect the presence of reaction products on the surface of the beads.

FIG. 9 shows a Microwell Array slide. As depicted, millions of microwells are microfabricated on the top surface of a microsubstrate. A fluidic manifold containing an inlet port, outlet port and a microwell is bonded to the microsubstrate containing the microwell array to form a composite microwell slide. A removeable heater lid allows all the microwells from accessible from the top surface.

Figure 11:
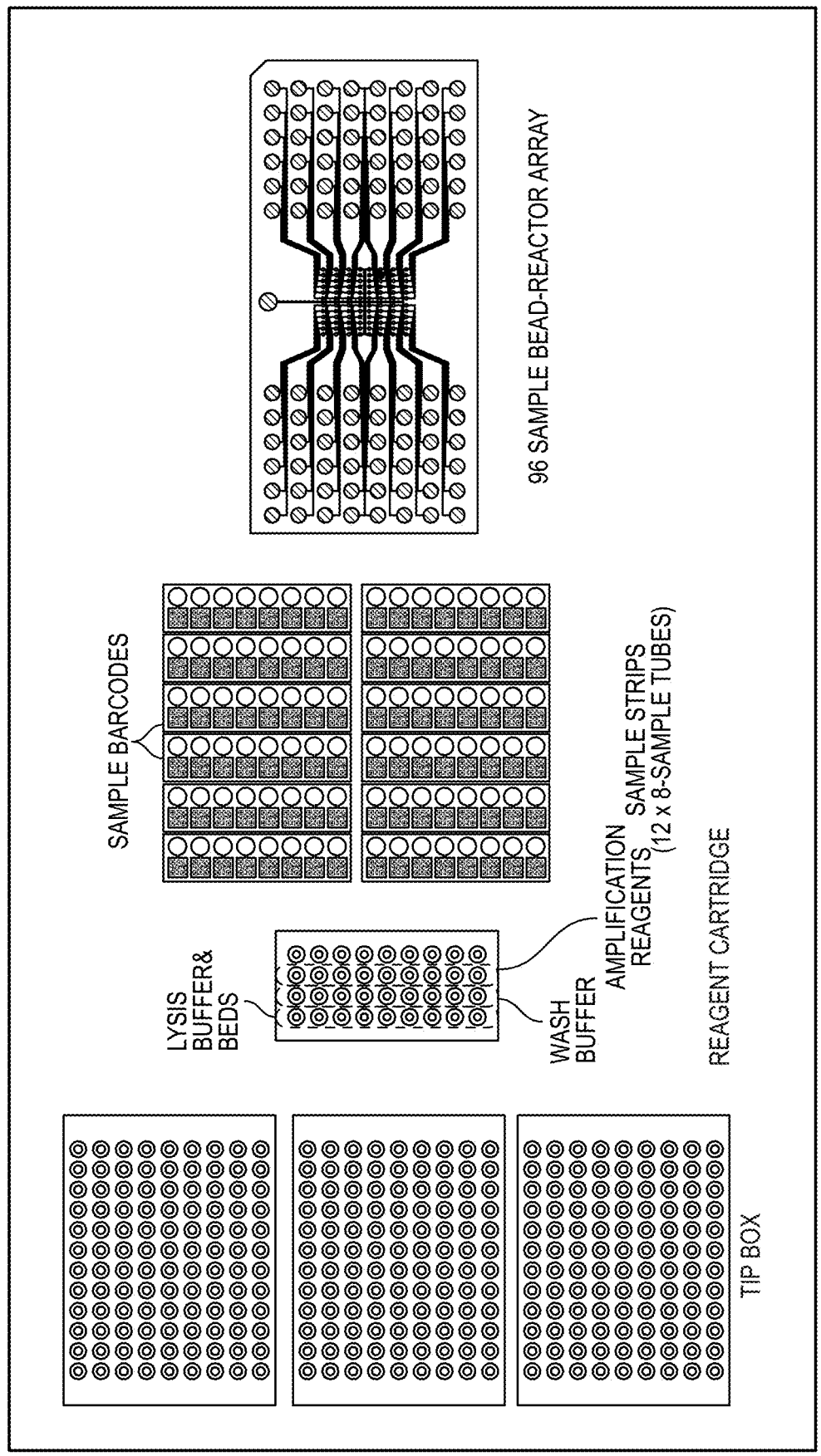
FIG. 11 shows the deck of the system showing various consumables used to process 96 clinical samples at the same time.
Figure 12:
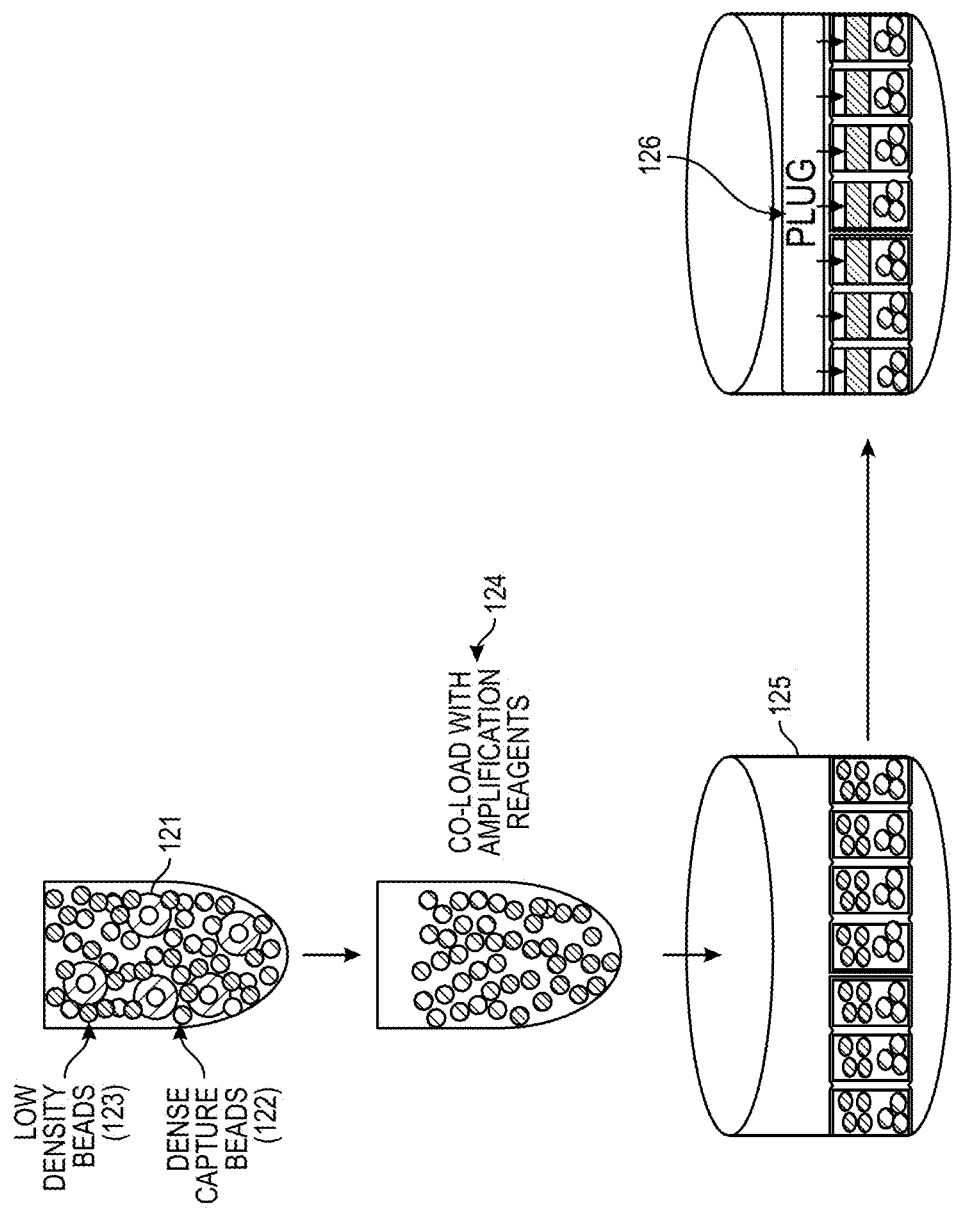
FIG. 12 depicts plugs for digital PCR. Viral particles (121) (or other targets) are mixed together with a slurry of high density capture beads (123) and low density beads (122). The low density beads (122) can be expandable with heat such as Expancel beads or sol-gel beads such as agarose that dissolve with a stimulus, e.g., heat, and solidify with removal of the stimulus. After capture of viral particles or RNA (or other targets) onto the dense capture beads, amplification reagents (124), such as those that support LAMP, are added. The entire bead slurry with the amplification reagents are added to the microwells (125). After bead settling, the stimulus is applied to create a plug (126) at the top of microwells. For example, Expancel beads will create a plug by heating the wells at 60° C. As another example, agarose beads will melt at temperatures higher than their Tm. Immediately cooling the well will cause them to form a plug. The amplification reaction occurs and the products are trapped in the wells by the plug. The high density capture beads can be substituted with magnetizable capture beads that allow them to be pulled down from the low solution to the bottom of the microwells by using an external magnet.
Figure 13:
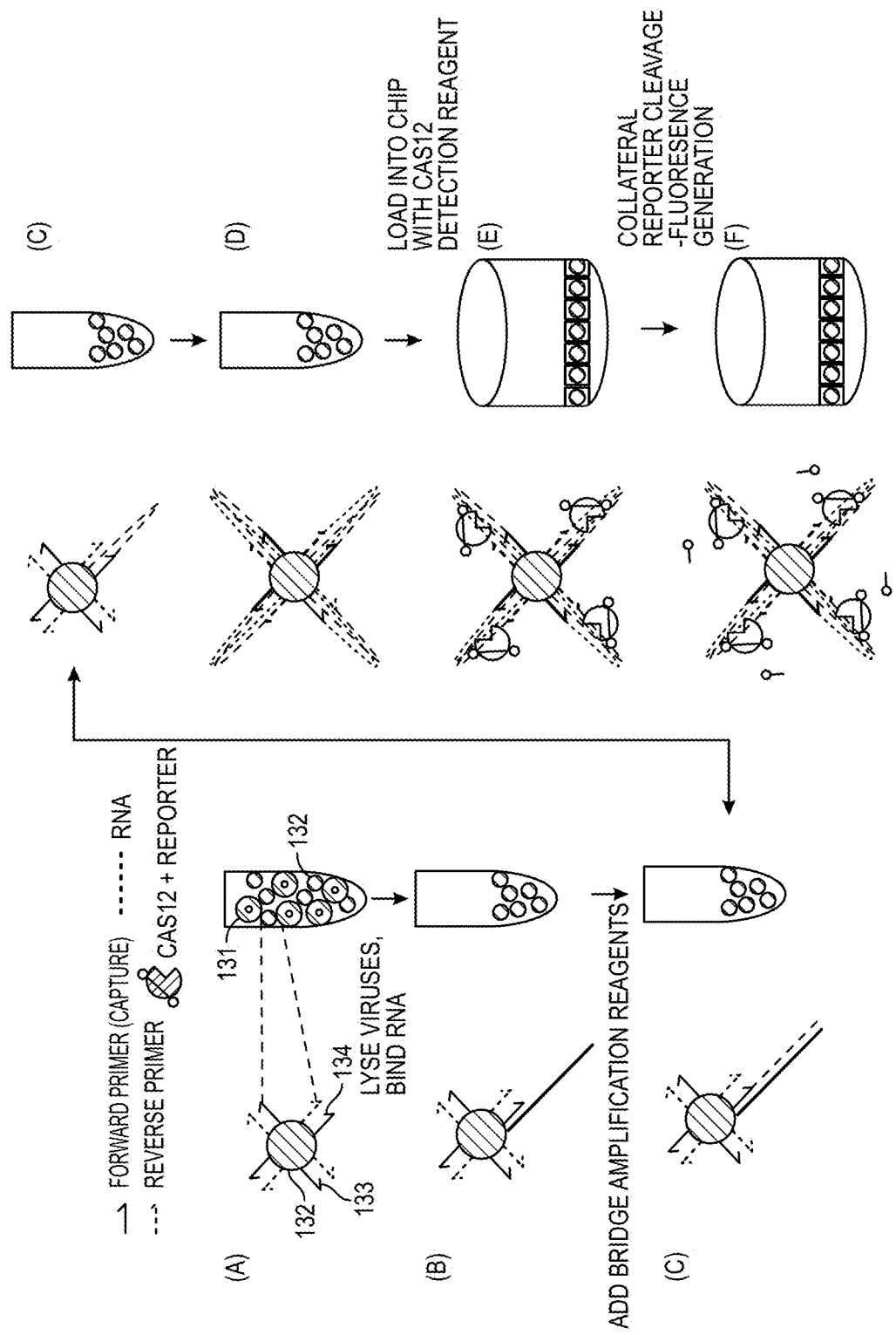
FIG. 13: Digital detection using CAS12. (A) Viral particles (131) (or other target nucleic acids) are mixed together with capture beads (132) and low density beads (not depicted). The capture beads contain both forward (133) and reverse (134) primers immobilized to the solid support. After viral lysis and capture of RNA (B) onto one of the two primers, such as the forward primer, on the capture beads, amplification reagents are added (C) and bridge amplification occurs (D) to create double stranded DNA. The CAS12 complex binds to the double stranded targets, is loaded into a chip with a Cas12 detection reagent (E) and resulting in collateral cleavage of a reporter molecule generating fluorescence (F).

FIG. 11 shows the deck of the instrument showing various consumables used to process 96 clinical samples at the same time. Exemplary consumables are
(a) Sample tubes
(b) A reagent cartridge containing lysis buffer-beads, wash buffer and amplification-detection reagents
(c) 96 sample bead-reactor array cartridge
(d) one or more tip boxes

EXAMPLE

Prophetic Example 1

The following can be performed using the system depicted for example in FIG. 5. A deck of an automated instrument used to process 96 samples at a time is prepared with the following:
A) Tip boxes
B) Reagent cartridge loaded with SSC (saline sodium citrate) based wash buffer, R(everse) T(ranscriptase) master mix, hotstart PCR master mix, primers and probes, PCR compatible oil and tips for loading these reagents into the Million Well Celsingle slide.
C) A 96 well plate containing viral lysis reagents and 20 micron polysterene oligo-dT(20)VN (SEQ ID NO: 1) beads. A universal tag sequence is positioned upstream of the oligo-dT track as shown below:
Bead Oligo Sequence:

(SEQ ID NO: 2)
5'-GCCTGTCCGCGGAAGCAGTGGTATCAACGCAGAGTACTTTTTTTT

TTTTTTTTTTTVN-3'

The viral lysis reagent contains the chaotropic salt guanidine thiocyanate and proteinase K. Each well is pre-loaded with approximately 10 000 beads. The beads are bound by a blocked fluorescent conjugated (FluorophoreX) reverse compliment oligo to the universal tag sequence:

(SEQ ID NO: 3)
FluorophoreX-GTACTCTGCGTTGATACCACTGCTTCCGCGGACAG

GC-invertedT

D) A Million Well Celsingle slide.
The protocol for running the 96 samples is outlined below:
(a) Off chip, dry swabs are rinsed with up to 400 uL of sterile PBS for up to 96 samples.
(b) The clinical samples are loaded into the sample strips, each strip containing 8 tubes. Each sample tube has a unique barcode.
(c) The xyz gantry moves the camera over various consumables, checks for barcodes and determines that the deck has all necessary consumables loaded to process all 96 samples (d) The automated pipettor picks up tips from the tip box in groups of 8 and transfers approximately 100 μL of each sample from the sample tube to the 96 well plate containing the lysis reagents and beads (e) The pipettor drops the tips in the tip box and continues the operation for the next samples until all samples are transferred to the 96 well plate to initiate lysis and binding.
(f) The samples in the lysis buffer are incubated for 15 minutes to completely digest the material. At the end of lysis, the beads settle to the bottom of the tube by gravity.
(g) The supernatant is discarded.
(h) The pipettor resuspends the beads in wash buffer. The beads are allowed to settle to the bottom of the tube by gravity.
(i) Steps g-h are repeated twice.
(j) After the last wash the beads are resuspended in the RT master mix to synthesize cDNA during a 15 min incubation period.
(k) The beads are washed once using the pipettor and allowed to settle to the bottom of the tube.
(l) Using the pipettor, the PCR master mix is added.
(m) Primers and probes are added and mixed with the capture beads and the PCR master mix.
(n) The beads are then transferred to the Million well slide from the % well plate. During this process, the lid of the Million Well slide is kept open such that the microwells are accessible from the top.
(o) After all beads (10,000 beads per sample) from 96 samples are dispensed in the Million well slide, the beads are allowed to settle into the microwells. The pipettor may be used to cause gentle agitation to promote all beads to be inserted into its microwell.
(p) The hinged lid of the Million Well Slide is closed using the pipettor using a lid opening/closing tool.
(q) Oil is then dispensed into the inlet port of the Million Well Slide to partition the microwells from each other.
(r) A heater in engaged on top of the lid to perform thermal incubations as required for the PCR amplification reaction. An elevated temperature occurs to initiate the reaction through hotstart of the PCR enzyme.
(s) At pre-determined time intervals, all the microwells are imaged in brightfield as well as fluorescence to monitor the progress of the amplification reaction using the 4-color fluorescence system.
(t) Using the processor and a pre-determined algorithm, the number of beads for each sample is determined to be positive and results for each sample is then displayed in a quantitative manner.

Prophetic Example 2

The following steps outline the use of the microwell slide of FIG. 9 during amplification and detection operation:
(1) The lid is kept open
(2) Beads are dispensed using a pipettor from the microwell.
(3) Allow the beads to settle into the microwells by gravity.
(4) Close the microwell using the heater-lid thereby forming a closed fluidic network.
(5) PCR reagent is dispensed into the inlet port allowing convective transport of PCR reagent through the microwells into the outlet. By way of diffusion, PCR reagents enter into the microwells.
(6) Oil is dispensed into the inlet port thereby covering the gap between the lid and the top surface of the microwell array, thereby physically partitioning the microwells from each other. PCR reagents present in the microwells are not displaced by the oil as reagents travel into the microwells only by diffusion and no convective currents penetrate into the microwell for oil to displace the aqueous reagents.

(7) Using the heater, PCR is performed and real-time detection using the fluorescence scanner.

Prophetic Example 3

The following can be performed using the system depicted for example in FIG. 11. The process for running 96 samples is outlined below:

(a) User loads clinical sample in sample strips. Each sample has a unique barcode. Samples can be loaded in strips of 8. A maximum of 96 samples can be loaded in the instrument.t
(b) User loads other consumables:
a. 96-sample bead-reactor array cartridge
b. Reagent cartridge
c. Tip boxes
(c) The xyz gantry moves the camera over various consumables, checks for barcodes and determines that the deck has all necessary consumables loaded to process all 96 samples.
(d) Outlet hole of the bead reactor array is initially in closed position.
(e) The pipettor picks up tips 1-8 from a tip box and pipets around 100 µl of lysis buffer containing beads (approx. 10,000 beads per sample) from the reagent cartridge and dispense them into the sample port 1-8 of the bead reactor array cartridge
(f) The pipettor than picks up 100 µl of sample from the sample tubes 1-8 and mixes them with the beads-lysis buffer present in the Bead Reactor Array position 1-8.
(g) The pipettor drops the tips in the tip box and continues the operation for the next samples until all samples are transferred to the 96 well plate to initiate lysis and binding.
(h) Wait approximately 10 minutes to allow for lysis and binding of target nucleic acids to the beads.
(i) The outlet port is pulled with certain vacuum pressure to cause all the fluid sample to move towards the bead reactor array thereby trapping the beads in the bead reactor.
(j) Wash is added to each of the wells of the 96 well plate and wash pulled through the bead reactor array to remove any unbound materials
(k) PCR reagents (Amplification and Detection reagents) are added to each of the sample inlets of the Bead Reactor Array Cartridge.
(l) Heater associated with the bead reactor array is turned on to incubate/thermocycle the reactor contents through the reaction protocol. The reaction products are amplified on the surface of each bead.
(m) At pre-determined time intervals, all the microwells are imaged in brightfield as well as fluorescence to monitor the progress of the amplification reaction using the 4-color fluorescence system.
(n) Using the processor and a pre-determined algorithm, the number of beads for each sample is determined to be positive and results for each sample is then displayed in a quantitative manner.

The above description of example embodiments of the invention has been presented for the purposes of illustration and description. It is not intended to be exhaustive or to limit the invention to the precise form described, and many modifications and variations are possible in light of the teaching above.

A recitation of "a," "an" or "the" is intended to mean "one or more" unless specifically indicated to the contrary. The use of "or" is intended to mean an "inclusive or," and not an "exclusive or" unless specifically indicated to the contrary.

EXAMPLE

This experiment demonstrates that beads can be used to bind DNA followed by bead-target delivery into microwells such that one bead is loaded per microwell. Well sealing, PCR amplification and fluorescent detection of amplified targets demonstrated that bead templated amplification in microwells occurred.

DNA-binding beads approximately 90 mm in diameter at 1000 beads/µL were mixed with 50 ng/µL genomic DNA and a hybridization solution containing Tris-EDTA and salt to provide high ionic strength was allowed to incubate for 15 minutes at room temperature. The beads were then washed to remove unbound DNA from the solution and placed in a PCR solution.

To isolate individual beads, the DNA-loaded beads were directly loaded via pipetting into chips that contain microwells. The plastic chip isolates individual beads in wells: Since the beads are 90 µm in diameter, and each well is a cube, with 100 µm long sides, only one bead can fit per well. When the chip is sealed via pressure from an elastomeric lid above, the beads are isolated in individual wells.

Bead-delivered DNA was thermal-amplified in individual microwells, using 45 cycles of PCR. Thermocycling was achieved on a flat plate heater, whose temperature was monitored and controlled.

Figure 14:
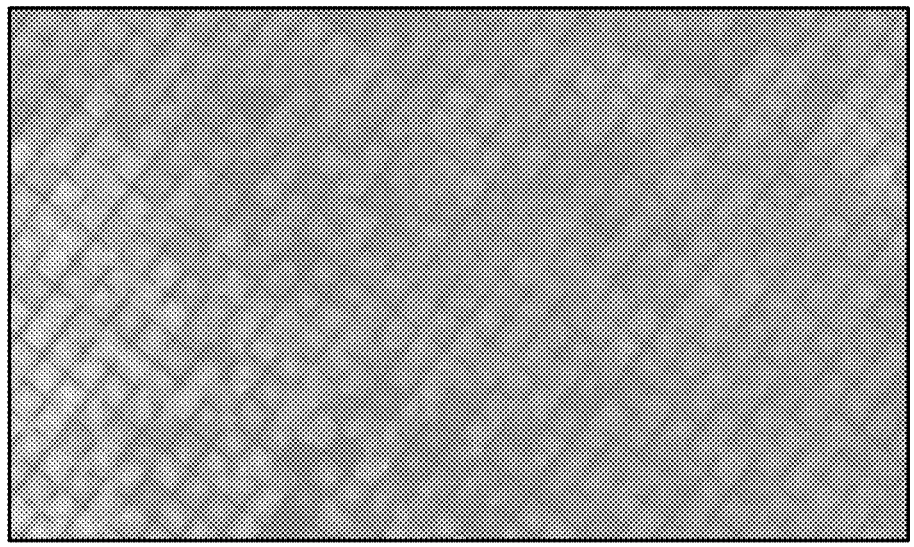
FIG. 14: Identification of DNA-positive wells post-amplification through fluorescent imaging. (Top) HEX image. The wells containing beads can be observed and denoted. (Bottom) Cy5 image. Wells that were loaded with DNA-positive beads became fluorescent after 45 cycles of PCR as the probe was hydrolyzed by the PCR polymerase.
Figure 14:
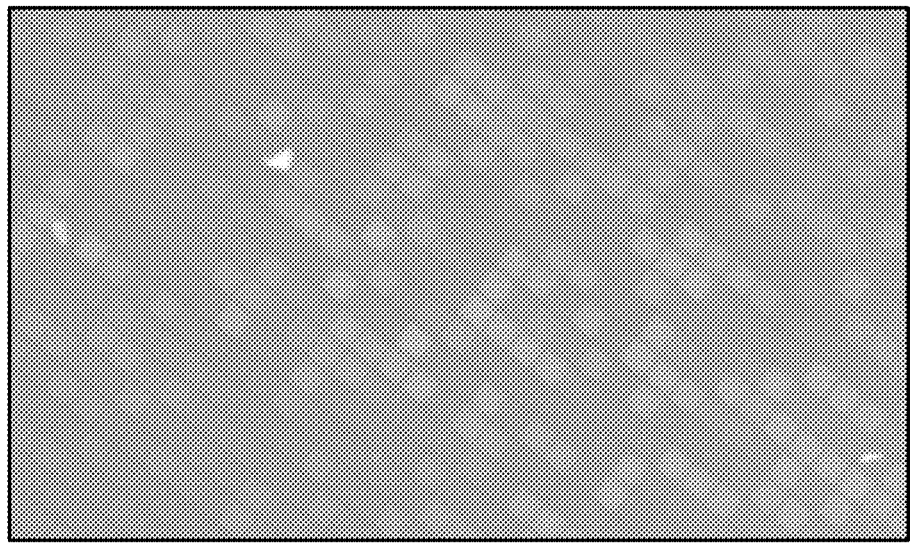

Detection of amplified DNA was achieved with probe amplification-dependent hydrolysis, which resulted in fluorescence in Cy5. FIG. 14 depicts the slide imaged using the HEX and the Cy5 channels to detect which wells had beads and which wells had undergone bead templated amplification, respectively.

By comparing the relative presence of illuminated versus dark wells, amplification positive wells can be scored, and the DNA can be quantified using Poisson statistics providing the DNA concentration in the original solution. Visualization of bead-free wells allows the exclusion of these wells from the analysis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. None is admitted to be prior art.

What is claimed is:

1. A method of detecting a target nucleic acid in multiple samples, the method comprising
   contacting different samples comprising sample nucleic acids, optionally contained in vehicles, with different pluralities of solid supports to form different mixtures, wherein the solid supports comprise a plurality of capture molecules that bind to the sample target nucleic acids or vehicles comprising the sample target nucleic acid, optionally wherein the plurality of capture molecules on a solid support are identical, and
   wherein the solid supports contacted to different samples have a characteristic distinguishable from other solid supports contacted to different samples;
   binding the capture molecules to the sample target nucleic acids or vehicles comprising the target nucleic acids, wherein the number of solid supports in the mixture is sufficiently high that at least some solid supports are not bound to target nucleic acids or vehicles comprising target nucleic acids;
   combining the different mixtures to form a bulk mixture;
   introducing the solid supports comprising bound sample target nucleic acids or vehicles into an array of wells, wherein the wells each can contain one but no more than one solid support;
   detecting in each well (i) the presence or absence of the sample target nucleic acids and (ii) the characteristic of the solid support, wherein the detecting is performed with a scanner; and
   determining with a computer processor the number of sample target nucleic acids per sample wherein the determining comprises determining the number of wells having detected sample target nucleic acids, wherein the sample identity is determined by the detected characteristic of the solid support.

2. The method of claim 1, wherein after the binding and before or after the combining, washing unbound sample components from the solid supports.

3. The method of claim 1, wherein the wells comprise affinity agents that bind the sample target nucleic acids or vehicles comprising sample target nucleic acids to the well.

4. The method of claim 1, wherein after the introducing, covering the wells.

5. The method of claim 4, further comprising amplifying the sample target nucleic acids.

6. The method of claim 5, wherein after the sample target nucleic acids are amplified, the sample target nucleic acids are attached to the wells via an affinity agent linked to the wells.

7. The method of claim 1, wherein the characteristic is the color of the solid support.

8. The method of claim 1, wherein the capture molecules are capture oligonucleotides and the binding comprises hybridizing the capture oligonucleotides to the sample target nucleic acids and following the introducing and before the detecting, amplifying the sample target nucleic acids hybridized to the capture oligonucleotides, and wherein the detecting comprises detecting signal from a reagent in the wells that changes based on the presence or absence of amplified nucleic acids.

9. The method of claim 1, wherein the sample target nucleic acids are RNA.

10. The method of claim 9, wherein the RNA is reverse transcribed into cDNA.

11. The method of claim 10, further comprising reverse transcribing the RNA before the introducing.

12. The method of claim 10, further comprising reverse transcribing the RNA after the introducing.

13. The method of claim 1, wherein the array of wells are of multiple different sizes or volumes.

14. The method of claim 13, wherein the solid supports are beads having diameters no less than 10% smaller than the diameter of well openings.

15. The method of claim 1, wherein the ratio of the diameter of the solid support to the diameter of the well is 1:1, or 1:2, or 1:3, or 1:4.

16. The method of claim 1, wherein sets of wells are separated from each other such that individual samples can be deposited in each.

17. The method of claim 1, wherein the solid supports contacted to the sample are of at least two types, wherein a first type comprises capture molecules that bind to a first sample target nucleic acid or a vehicle comprising the first sample target nucleic acid and a second type comprises capture molecules that bind to a second sample target nucleic acid or a vehicle comprising the second sample target nucleic acid.

18. The method of claim 1, wherein the capture molecules are oligonucleotides complementary to the sample target nucleic acid and the binding comprises hybridization.

19. A method of detecting a target nucleic acid in multiple samples, the method comprising
contacting different samples comprising sample nucleic acids with different pluralities of solid supports to form different mixtures, wherein the solid supports comprise a plurality of capture molecules that bind to the sample target nucleic acid or a vehicle comprising the sample target nucleic acid, optionally wherein the plurality of capture molecules on a solid support are identical;
binding the capture molecules to the sample target nucleic acids, wherein the number of solid supports in the mixture is sufficiently high that at least some solid supports are not bound to target nucleic acids or vehicles comprising target nucleic acids;
introducing the solid supports comprising bound sample target nucleic acids or vehicles comprising sample target nucleic acids into an array of wells, wherein the wells each can contain no more than one solid support, wherein the position of wells receiving the sample beads is recorded such that wells corresponding to different samples is recorded;
detecting in each well (i) the presence or absence of the sample target nucleic acids and (ii) the position of the wells, wherein the detecting is performed with a scanner; and
determining with a computer processor the number of sample target nucleic acids per sample based in part on the number of wells comprising detected sample target nucleic acids, wherein the sample identity is determined by the position of the wells.

20. A method of detecting a target nucleic acid in multiple samples, the method comprising
contacting different samples comprising sample nucleic acids, optionally contained in vehicles, with different pluralities of solid supports to form different mixtures, wherein the solid supports comprise a plurality of capture molecules that bind to the sample target nucleic acids or a vehicles comprising the sample target nucleic acid, optionally wherein the plurality of capture molecules on a solid support are identical, and
wherein the solid supports contacted to different samples have a characteristic distinguishable from other solid supports contacted to different samples;
binding the capture molecules to the sample target nucleic acids or vehicles comprising the target nucleic acids, wherein the number of solid supports in the mixture is sufficiently high that at least some solid supports are not bound to target nucleic acids or vehicles comprising target nucleic acids;
combining the different mixtures to form a bulk mixture;
introducing the solid supports comprising bound sample target nucleic acids or vehicles into an array of wells, wherein the wells can contain more than one solid support;
detecting in each well (i) the presence and intensity or absence of signal indicative of the sample target nucleic acids and (ii) the characteristic of the solid support, wherein the detecting is performed with a scanner; and
determining with a computer processor the number of sample target nucleic acids per sample wherein the determining comprises determining the number of wells having detected sample target nucleic acids and different signal intensities between wells together with the presence or absence of signal in each well is used to measure the concentration of target molecules in a sample, and wherein the sample identity is determined by the detected characteristic of the solid support.

* * * * *

SEQUENCE LISTING

<160> NUMBER OF SEQ ID NOS: 3

<210> SEQ ID NO 1

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(22)
<223> OTHER INFORMATION: a, c, t, g, unknown or other

<400> SEQUENCE: 1
tttttttttt tttttttttt vn                                             22

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (59)..(59)
<223> OTHER INFORMATION: a, c, t, g, unknown or other

<400> SEQUENCE: 2
gcctgtccgc ggaagcagtg gtatcaacgc agagtacttt tttttttttt tttttttvn     59

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: inverted thymine

<400> SEQUENCE: 3
gtactctgcg ttgataccac tgcttccgcg gacaggct                            38
```